United States Patent
Pozueta Romero et al.

(10) Patent No.: US 7,338,776 B2
(45) Date of Patent: Mar. 4, 2008

(54) PRODUCTION OF UGPPASE

(75) Inventors: Javier Pozueta Romero, Navarra (ES); Edurne Baroja Fernandez, Navarra (ES); Francisco Jose Munoz, Navarra (JP); Imbak Shu, Hyogo (JP); Ryuji Yamamoto, Hyogo (JP)

(73) Assignees: JCR Pharmaceuticals Co., Ltd., Ashiya-shi (JP); Universidad Publica De Navarra Campus Arrosadia, Navarra (ES)

( * ) Notice: Subject to any disclaimer, the term of this patent is extended or adjusted under 35 U.S.C. 154(b) by 0 days.

(21) Appl. No.: 10/508,312

(22) PCT Filed: Mar. 17, 2003

(86) PCT No.: PCT/JP03/03189

§ 371 (c)(1),
(2), (4) Date: Jun. 16, 2005

(87) PCT Pub. No.: WO03/078618

PCT Pub. Date: Sep. 25, 2003

(65) Prior Publication Data

US 2006/0073533 A1  Apr. 6, 2006

(30) Foreign Application Priority Data

Mar. 20, 2002 (JP) ............... PCT/JP02/02726
Sep. 17, 2002 (JP) ............... PCT/JP02/09542

(51) Int. Cl.
*C12Q 1/34* (2006.01)
*C12Q 1/68* (2006.01)
*C12N 9/24* (2006.01)
*C12N 11/00* (2006.01)
*C12N 15/70* (2006.01)
*C12N 5/00* (2006.01)
*C07H 21/06* (2006.01)

(52) U.S. Cl. ................ 435/18; 435/6; 435/200; 435/174; 435/69.1; 435/320.1; 435/325; 436/23.2

(58) Field of Classification Search ............. 435/199, 435/7.92, 388.26
See application file for complete search history.

(56) References Cited

OTHER PUBLICATIONS

Yagi et al. Cloning, expression and characterization of a mammalian Nudix hydrolase-like enzyme that cleaves the pyrophosphate bond of UDP-glucose. Biochem J. Mar. 1, 2003(Pt 2):409-15.*
Database EMBL 'Online! EBI; Hypothetical protein, May 1, 1999 retrieved from EMBL Database accession No. 095848.
Bachorik P S et al: "The Purification and Properties of Detergent Solubilized Rat Liver Nucleotide Pyro Phosphatase" Journal of Biological Chemistry, vol. 247, No. 16, pp. 5071-5078.
Skidmore J R et al.: "Nucleotide Pyro Phosphatase EC-3.6.1.9 Activity of Rat Liver Plasma Membranes" Biochimica et Biophysica Acta, vol. 219, No. 1, 1970, pp. 93-103.
Schlisefeld L H et al: "The Purification and Properties of a Nucleotide Pyrophosphatase of Rat Liver Nuclei" The Journal of Biological Chemistry, vol. 240, No. 2, Feb. 1995, pp. 811-818.
Guranowski Andrzej: "Specific and nonspecific enzymes involved in the catabolism of mononucleoside and dinucleoside polyphosphates." Pharmacology & Therapeutics, vol. 87, No. 2-3, Aug. 2000, pp. 117-139.
Bessman M J et al.: "The MutT proteins or Nudix hydrolases, a family of versatile, widely distributed, housecleaning enzymes" Journal of Biological Chemistry, American Society of Biological Chemists, vol. 271, No. 41, Oct. 11, 1996, pp. 25059-25062.
McLennman A G: "The Mut Motif Family of Nucleotide Phosphohydrolases in Man and Human Pathogens (Review)" International Journal of Molecular Medicine, vol. 4, No. 1, 1999, pp. 79-89.

* cited by examiner

*Primary Examiner*—Rebecca E. Prouty
*Assistant Examiner*—Iqbal Chowdhury
(74) *Attorney, Agent, or Firm*—Miller, White, Zelano, Branigan, P.C.

(57) ABSTRACT

A purified novel enzyme protein, UGPPase, which naturally occurs in animal cells, its productions of recombinant technology, an antibody to the enzyme protein, a method of carrying out ELISA for measurement of the amount of UGPPase in an analyte and a method for determination of UDPG in a sample. The one-way enzyme protein catalyses hydrolysis of UDP-glucose, the precursor molecule of glycogen, into glucose-1-phosphate (G1P) and uridine 5'-monophosphate (UMP).

13 Claims, 17 Drawing Sheets

```
human a.a.:   1 Met Gly Leu Leu Leu Pro Leu Pro Val Pro Gly Leu Leu Leu Leu Glu Ala  17 human a.a.:  18 Glu Thr His Pro His Phe Pro Cys Asn His Gly Gln Glu Gly Ala Cys Thr  34 human a.a.:  35 Arg His Ala Arg Val Arg Ala Tyr Pro Gly Pro Leu Val His Arg Arg Lys  51 human a.a.:  52 Arg Pro Ala Trp Leu Trp Glu Leu Ala Ala Pro Ala Cys Pro Gly Ala Ala  68 human a.a.:  69 Met Glu Arg Ile Glu Gly Ala Ser Val Gly Arg Cys Ala Ala Ser Pro Tyr  85
mouse a.a.:   1 Met Glu Arg Ile Asp Gly Val Ala Val Gly Leu Cys Ala His Ser Pro Tyr  17 human a.a.:  86 Leu Arg Pro Leu Thr Leu His Tyr Arg Gln Asn Gly Ala Gln Lys Ser Trp 102
mouse a.a.:  18 Leu Arg Pro Phe Thr Leu His Tyr Arg Gln Asp Gly Val Gln Lys Ser Trp  34 human a.a.: 103 Asp Phe Met Lys Thr His Asp Ser Val Thr Val Leu Leu Phe Asn Ser Ser 119
mouse a.a.:  35 Asp Phe Met Lys Thr His Asp Ser Val Thr Ile Leu Met Phe Asn Ser Ser  51
pig a.a.:                       Thr His Asp Ser Val Thr Ile Leu Met Phe Asn Ala Ser human a.a.: 120 Arg Arg Ser Leu Val Leu Val Lys Gln Phe Arg Pro Ala Val Tyr Ala Gly 136
mouse a.a.:  52 Arg Arg Ser Leu Val Leu Val Lys Gln Phe Arg Pro Ala Val Tyr Ala Gly  68
pig a.a.:        Arg human a.a.: 137 Glu Val Glu Arg Arg Phe Pro Gly Ser Leu Ala Ala Val Asp Gln Asp Gly 153
mouse a.a.:  69 Glu Val Glu Arg His Phe Pro Gly Ser Leu Thr Ala Val Asn Gln Asp Gln  85
pig a.a.:                            Pro Gly Ser Leu Val Ala Ala Asn Gln Asp Arg human a.a.: 154 Pro Arg Glu Leu Gln Pro Ala Leu Pro Gly Ser Ala Gly Val Thr Val Glu 170
mouse a.a.:  86 Pro Gln Glu Leu Gln Gln Ala Leu Pro Gly Ser Ala Gly Val Met Val Glu 102
pig a.a.:        Pro Arg
```

Fig. 6

```
human a.a.: 171 Leu Cys Ala Gly Leu Val Asp Gln Pro Gly Leu Ser Leu Glu Glu Val Ala 187
mouse a.a.: 103 Leu Cys Ala Gly Ile Val Asp Gln Pro Gly Leu Ser Leu Glu Glu Ala Ala 119 human a.a.: 188 Cys Lys Glu Ala Trp Glu Glu Cys Gly Tyr His Leu Ala Pro Ser Asp Leu 204
mouse a.a.: 120 Cys Lys Glu Ala Trp Glu Glu Cys Gly Tyr Arg Leu Val Pro Thr Asp Leu 136 human a.a.: 205 Arg Arg Val Ala Thr Tyr Trp Ser Gly Val Gly Leu Thr Gly Ser Arg Gln 221
mouse a.a.: 137 Arg Arg Val Ala Thr Tyr Met Ser Gly Val Gly Leu Thr Ser Ser Arg Gln 153 human a.a.: 222 Thr Met Phe Tyr Thr Glu Val Thr Asp Ala Gln Arg Ser Gly Pro Gly Gly 238
mouse a.a.: 154 Thr Met Phe Tyr Ala Glu Val Thr Asp Ala Gln Arg Gly Gly Pro Gly Gly 170
  pig a.a.:     Tyr Met Phe Tyr Ala Ala Val Thr Asp Ala Gln Arg human a.a.: 239 Gly Leu Val Glu Glu Gly Glu Leu Ile Glu Val Val His Leu Pro Leu Glu 255
mouse a.a.: 171 Gly Leu Ala Glu Glu Gly Glu Leu Ile Glu Val Ile His Leu Asn Leu Asp 187 human a.a.: 256 Gly Ala Gln Ala Phe Ala Asp Asp Pro Asp Ile Pro Lys Thr Leu Gly Val 272
mouse a.a.: 188 Asp Ala Gln Ala Phe Ala Asp Asn Pro Asp Ile Pro Lys Thr Leu Gly Val 204
  pig a.a.:         Gln Ala Phe Ala Asp Asp Ser human a.a.: 273 Ile Phe Gly Val Ser Trp Phe Leu Ser Gln Val Ala Pro Asn Leu Asp Leu 289
mouse a.a.: 205 Ile Tyr Ala Ile Ser Trp Phe Phe Ser Gln Val Val Pro His Leu Ser Leu 221 human a.a.: 290 Gln
mouse a.a.: 222 Gln
```

Fig. 7

SEQUENCE LISTING

```
<160> NUMBER OF SEQ ID NOS: 12

<210> SEQ ID NO 1
<211> LENGTH: 669
<212> TYPE: DNA
<213> ORGANISM: Homo sapiens
<220> FEATURE:
<223> OTHER INFORMATION: cDNA coding for USPPase

<400> SEQUENCE: 1 atg gag cgc atc gag ggg gcg tcc gtg ggc cgc tgc gcc gcc tca ccc      48
Met Glu Arg Ile Glu Gly Ala Ser Val Gly Arg Cys Ala Ala Ser Pro
 1               5                  10                  15 tac ctg cgg ccg ctc acg ctg cat tac cgc cag aat ggt gcc cag aag      96
Tyr Leu Arg Pro Leu Thr Leu His Tyr Arg Gln Asn Gly Ala Gln Lys
             20                  25                  30 tcc tgg gac ttc atg aag acg cat gac agc gtg acc gtt ctc tta ttc     144
Ser Trp Asp Phe Met Lys Thr His Asp Ser Val Thr Val Leu Leu Phe
         35                  40                  45 aac tct tct cgg agg agc ctg gtg ttg gtg aag cag ttc cgg cca gct     192
Asn Ser Ser Arg Arg Ser Leu Val Leu Val Lys Gln Phe Arg Pro Ala
     50                  55                  60 gtg tat gcg ggt gag gtg gag cgc cgc ttc cca ggg tcc cta gca gct     240
Val Tyr Ala Gly Glu Val Glu Arg Arg Phe Pro Gly Ser Leu Ala Ala
 65                  70                  75                  80 gta gac cag gac ggg cct cgg gag cta cag cca gcc ctg ccc ggc tca     288
Val Asp Gln Asp Gly Pro Arg Glu Leu Gln Pro Ala Leu Pro Gly Ser
                 85                  90                  95
```

```
gcg ggg gtg aca gtt gag ctg tgt gcc ggc ctc gtg gac cag cct ggg      336
Ala Gly Val Thr Val Glu Leu Cys Ala Gly Leu Val Asp Gln Pro Gly
            100                 105                 110 ctc tcg ctg gag gaa gtg gct tgc aag gag gct tgg gag gag tgt ggc      384
Leu Ser Leu Glu Glu Val Ala Cys Lys Glu Ala Trp Glu Glu Cys Gly
        115                 120                 125 tac cac ttg gcc ccc tct gat ctg cgc cgg gtc gcc aca tac tgg tct      432
Tyr His Leu Ala Pro Ser Asp Leu Arg Arg Val Ala Thr Tyr Trp Ser
    130                 135                 140 gga gtg gga ctg act ggc tcc aga cag acc atg ttc tac aca gag gtg      480
Gly Val Gly Leu Thr Gly Ser Arg Gln Thr Met Phe Tyr Thr Glu Val
145                 150                 155                 160 aca gat gcc cag cgt agc ggt cca ggt ggg ggc ctg gtg gag gag ggt      528
Thr Asp Ala Gln Arg Ser Gly Pro Gly Gly Gly Leu Val Glu Glu Gly
                165                 170                 175 gag ctc att gag gtg gtg cac ctg ccc ctg gaa ggc gcc cag gcc ttt      576
Glu Leu Ile Glu Val Val His Leu Pro Leu Glu Gly Ala Gln Ala Phe
            180                 185                 190 gca gac gac ccg gac atc ccc aag acc ctc ggc gtc atc ttt ggt gtc      624
Ala Asp Asp Pro Asp Ile Pro Lys Thr Leu Gly Val Ile Phe Gly Val
        195                 200                 205 tca tgg ttc ctc agc cag gtg gcc ccc aac ctg gat ctc cag tga          669
Ser Trp Phe Leu Ser Gln Val Ala Pro Asn Leu Asp Leu Gln
    210                 215                 220

<210> SEQ ID NO 2
<211> LENGTH: 222
<212> TYPE: PRT
<213> ORGANISM: Homo sapiens
<220> FEATURE:
<223> OTHER INFORMATION: USPPase

<400> SEQUENCE: 2

Met Glu Arg Ile Glu Gly Ala Ser Val Gly Arg Cys Ala Ala Ser Pro
 1               5                  10                  15

Tyr Leu Arg Pro Leu Thr Leu His Tyr Arg Gln Asn Gly Ala Gln Lys
            20                  25                  30

Ser Trp Asp Phe Met Lys Thr His Asp Ser Val Thr Val Leu Leu Phe
        35                  40                  45

Asn Ser Ser Arg Arg Ser Leu Val Leu Val Lys Gln Phe Arg Pro Ala
    50                  55                  60

Val Tyr Ala Gly Glu Val Glu Arg Arg Phe Pro Gly Ser Leu Ala Ala
65                  70                  75                  80

Val Asp Gln Asp Gly Pro Arg Glu Leu Gln Pro Ala Leu Pro Gly Ser
                85                  90                  95

Ala Gly Val Thr Val Glu Leu Cys Ala Gly Leu Val Asp Gln Pro Gly
            100                 105                 110

Leu Ser Leu Glu Glu Val Ala Cys Lys Glu Ala Trp Glu Glu Cys Gly
        115                 120                 125

Tyr His Leu Ala Pro Ser Asp Leu Arg Arg Val Ala Thr Tyr Trp Ser
    130                 135                 140

Gly Val Gly Leu Thr Gly Ser Arg Gln Thr Met Phe Tyr Thr Glu Val
145                 150                 155                 160

Thr Asp Ala Gln Arg Ser Gly Pro Gly Gly Gly Leu Val Glu Glu Gly
                165                 170                 175

Glu Leu Ile Glu Val Val His Leu Pro Leu Glu Gly Ala Gln Ala Phe
            180                 185                 190
```

Ala Asp Asp Pro Asp Ile Pro Lys Thr Leu Gly Val Ile Phe Gly Val
            195                 200                 205

Ser Trp Phe Leu Ser Gln Val Ala Pro Asn Leu Asp Leu Gln
        210                 215                 220

<210> SEQ ID NO 3
<211> LENGTH: 290
<212> TYPE: PRT
<213> ORGANISM: Homo sapiens
<220> FEATURE:
<223> OTHER INFORMATION: Protein ID number AAD15563.1

<400> SEQUENCE: 3

Met Gly Leu Leu Leu Pro Leu Pro Val Pro Gly Leu Leu Leu Leu Glu
  1               5                  10                  15

Ala Glu Thr His Pro His Phe Pro Cys Asn His Gly Gln Glu Gly Ala
                20                  25                  30

Cys Thr Arg His Ala Arg Val Arg Ala Tyr Pro Gly Pro Leu Val His
            35                  40                  45

Arg Arg Lys Arg Pro Ala Trp Leu Trp Glu Leu Ala Ala Pro Ala Cys
        50                  55                  60

Pro Gly Ala Ala Met Glu Arg Ile Glu Gly Ala Ser Val Gly Arg Cys
 65                  70                  75                  80

Ala Ala Ser Pro Tyr Leu Arg Pro Leu Thr Leu His Tyr Arg Gln Asn
                85                  90                  95

Gly Ala Gln Lys Ser Trp Asp Phe Met Lys Thr His Asp Ser Val Thr
                100                 105                 110

Val Leu Leu Phe Asn Ser Ser Arg Arg Ser Leu Val Leu Val Lys Gln
            115                 120                 125

Phe Arg Pro Ala Val Tyr Ala Gly Glu Val Glu Arg Arg Phe Pro Gly
        130                 135                 140

Ser Leu Ala Ala Val Asp Gln Asp Gly Pro Arg Glu Leu Gln Pro Ala
145                 150                 155                 160

Leu Pro Gly Ser Ala Gly Val Thr Val Glu Leu Cys Ala Gly Leu Val
                165                 170                 175

Asp Gln Pro Gly Leu Ser Leu Glu Glu Val Ala Cys Lys Glu Ala Trp
            180                 185                 190

Glu Glu Cys Gly Tyr His Leu Ala Pro Ser Asp Leu Arg Arg Val Ala
        195                 200                 205

Thr Tyr Trp Ser Gly Val Gly Leu Thr Gly Ser Arg Gln Thr Met Phe
    210                 215                 220

Tyr Thr Glu Val Thr Asp Ala Gln Arg Ser Gly Pro Gly Gly Leu
225                 230                 235                 240

Val Glu Glu Gly Glu Leu Ile Glu Val His Leu Pro Leu Glu Gly
                245                 250                 255

Ala Gln Ala Phe Ala Asp Asp Pro Asp Ile Pro Lys Thr Leu Gly Val
            260                 265                 270

Ile Phe Gly Val Ser Trp Phe Leu Ser Gln Val Ala Pro Asn Leu Asp
        275                 280                 285

Leu Gln
    290

<210> SEQ ID NO 4
<211> LENGTH: 222
<212> TYPE: PRT
<213> ORGANISM: Mus musculus
<220> FEATURE:

<223> OTHER INFORMATION: Protein ID number BAB23110.1

<400> SEQUENCE: 4

```
Met Glu Arg Ile Asp Gly Val Ala Val Gly Leu Cys Ala His Ser Pro
 1               5                  10                  15

Tyr Leu Arg Pro Phe Thr Leu His Tyr Arg Gln Asp Gly Val Gln Lys
            20                  25                  30

Ser Trp Asp Phe Met Lys Thr His Asp Ser Val Thr Ile Leu Met Phe
        35                  40                  45

Asn Ser Ser Arg Arg Ser Leu Val Leu Val Lys Gln Phe Arg Pro Ala
    50                  55                  60

Val Tyr Ala Gly Glu Val Glu Arg His Phe Pro Gly Ser Leu Thr Ala
65                  70                  75                  80

Val Asn Gln Asp Gln Pro Gln Glu Leu Gln Ala Leu Pro Gly Ser
                85                  90                  95

Ala Gly Val Met Val Glu Leu Cys Ala Gly Ile Val Asp Gln Pro Gly
                100                 105                 110

Leu Ser Leu Glu Glu Ala Ala Cys Lys Glu Ala Trp Glu Glu Cys Gly
            115                 120                 125

Tyr Arg Leu Val Pro Thr Asp Leu Arg Arg Val Ala Thr Tyr Met Ser
        130                 135                 140

Gly Val Gly Leu Thr Ser Ser Arg Gln Thr Met Phe Tyr Ala Glu Val
145                 150                 155                 160

Thr Asp Ala Gln Arg Gly Gly Pro Gly Gly Gly Leu Ala Glu Glu Gly
                165                 170                 175

Glu Leu Ile Glu Val Ile His Leu Asn Leu Asp Asp Ala Gln Ala Phe
            180                 185                 190

Ala Asp Asn Pro Asp Ile Pro Lys Thr Leu Gly Val Ile Tyr Ala Ile
        195                 200                 205

Ser Trp Phe Phe Ser Gln Val Val Pro His Leu Ser Leu Gln
    210                 215                 220
```

<210> SEQ ID NO 5
<211> LENGTH: 14
<212> TYPE: PRT
<213> ORGANISM: Sus scrofa
<220> FEATURE:
<223> OTHER INFORMATION: peptide fragment of USPPase

<400> SEQUENCE: 5

```
Thr His Asp Ser Val Thr Ile Leu Met Phe Asn Ala Ser Arg
 1               5                  10
```

<210> SEQ ID NO 6
<211> LENGTH: 13
<212> TYPE: PRT
<213> ORGANISM: Sus scrofa
<220> FEATURE:
<223> OTHER INFORMATION: peptide fragment of USPPase

<400> SEQUENCE: 6

```
Pro Gly Ser Leu Val Ala Ala Asp Gln Asp Arg Pro Arg
 1               5                  10
```

<210> SEQ ID NO 7
<211> LENGTH: 12
<212> TYPE: PRT
<213> ORGANISM: Sus scrofa
<220> FEATURE:
<223> OTHER INFORMATION: peptide fragment of porcine USPPase

```
<400> SEQUENCE: 7

Tyr Met Phe Tyr Ala Ala Val Thr Asp Ala Gln Arg
 1               5                  10

<210> SEQ ID NO 8
<211> LENGTH: 7
<212> TYPE: PRT
<213> ORGANISM: Sus scrofa
<220> FEATURE:
<223> OTHER INFORMATION: peptide fragment of porcine USPPase

<400> SEQUENCE: 8

Gln Ala Phe Ala Asp Asp Ser
 1               5

<210> SEQ ID NO 9
<211> LENGTH: 29
<212> TYPE: DNA
<213> ORGANISM: Artificial Sequence
<220> FEATURE:
<223> OTHER INFORMATION: primer sequence having at its 5' end an NdeI
      cleavage site

<400> SEQUENCE: 9
catatggagc gcatcgaggg ggcgtccgt                                     29

<210> SEQ ID NO 10
<211> LENGTH: 32
<212> TYPE: DNA
<213> ORGANISM: Artificial Sequence
<220> FEATURE:
<223> OTHER INFORMATION: primer sequence having at its 5' end an BamHI
      cleavage site

<400> SEQUENCE: 10
ggatcctcac tggagatcca ggttgggggc ca                                 32

<210> SEQ ID NO 11
<211> LENGTH: 21
<212> TYPE: DNA
<213> ORGANISM: Artificial Sequence
<220> FEATURE:
<223> OTHER INFORMATION: T7 primer

<400> SEQUENCE: 11
tctaatacga ctcactatag g                                             21

<210> SEQ ID NO 12
<211> LENGTH: 17
<212> TYPE: DNA
<213> ORGANISM: Artificial Sequence
<220> FEATURE:
<223> OTHER INFORMATION: M13 primer M4

<400> SEQUENCE: 12
gttttcccag tcacgac                                                  17
```

PRODUCTION OF UGPPASE

TECHNICAL FIELD

The present invention relates to UDP-glucose pyrophosphatase (UGPPase), a novel enzyme protein found to occur in animals, and to the preparation of the protein in a purified form, as well as to the uses of the protein in the field of biochemical analysis including ELISA and for the determination of UDP-glucose contained in a sample.

BACKGROUND ART

Glycogen is a polysaccharide that is the major carbohydrate in animal cells and a variety of bacteria including *Escherichia coli*, just like starch is in plants. Starch in plants and glycogen in bacteria are produced from a common substrate, ADPglucose (ADPG). In animals, on the other hand, glycogen is synthesized from UDP-glucose (UDPG) (1). The net rate of the synthesis of those storage polysaccharides in organisms is thought to be controlled by a variety of regulatory factors that respond to external environment as well as to internal physiological conditions. Such regulatory factors are expected to act, for example, in allosteric control of the reaction of ADPG (or UDPG) pyrophosphorylase (AGPase or UGPase, respectively) in the glycogenesis pathway, or by controlling the expression of genes coding for gluconeogenic enzymes (1-4).

Recent investigations have demonstrated that glycogen can be simultaneously synthesized and degraded during bacterial growth, thus making up a futile cycle wherein AGPase has a dual role in catalyzing the de novo synthesis of ADPG and in recycling the glucose units derived from the glycogen breakdown (5-7).

Simultaneous synthesis and degradation of glycogen and starch have been reported to occur also in animals and plants, respectively (8-10), thus indicating that the operation of futile cycling may entail advantages such as sensitive regulation and channelling of excess gluconeogenic intermediates toward various metabolic pathways in response to physiological and biochemical needs.

Presence of a one-way enzyme that catalyzes hydrolysis of ADPG (or UDPG) had been predicted in connection with this futile cycle-like route, which would allow more sensitive regulation of ADPG (UDPG) levels and therefore of the net rate of synthesis/degradation of storage polysaccharides. The first of such enzymes was discovered by Pozueta-Romero, J. and co-workers, who isolated and purified ADP-glucose pyrophosphatase (AGPPase) from barley and bacteria (11-13). The AGPPase they isolated was a one-way enzyme catalyzing hydrolysis of ADPG to glucose-1-phosphate (G1P) and adenosine 5'-monophosphate (AMP). Enzymes catalyzing the hydrolytic breakdown of UDPG have been reported to occur in mammalian cells (14-16). Playing a role in the control of glycoprotein, glycolipid and glycosaminoglycan biosynthesis (17-22), these enzymes show broad substrate specificity and have been found to be associated with nuclear, mitochondrial, endoplasmic reticulum and plasma membrane fractions.

Glycogen biosynthesis takes place in the cytosol. The possible involvement of enzymatic breakdown of UDPG in the control of carbon flow towards glycogen in mammalian cells has prompted us to identify a cytosolic protein, designated as UDP-glucose pyrophosphatase (UGPPase), that hydrolyzes UDPG with substantially the highest specificity.

DISCLOSURE OF INVENTION

Now, applying a technique for purification of enzyme proteins, SDS-free PAGE (hereinafter referred to as "native PAGE"), the present inventors have successfully purified from animals (human and pig) UDP-glucose pyrophosphatase (UGPPase), an enzyme having properties comparable to those of AGPPase in plants and bacteria, and established a method for producing the enzyme by means of recombinant technology. This enzyme, now finally designated as UGPPase, is the enzyme that the inventors tentatively named UGPPase or USPPase as disclosed in their international applications PCT/JP02/02726, filed on Mar. 20, 2002 or PCT/JP02/09542, filed on Sep. 17, 2002, respectively.

UGPPase is a one-way hydrolysis enzyme that catalyzes conversion of UDPG, the precursor molecule of glycogen, to G1P and UMP.

Thus the present invention provides a purified enzyme protein comprising the amino acid sequence set forth as SEQ ID NO: 2 in the Sequence Listing. The protein has the UGPPase activity, i.e., the activity of hydrolyzing UDP-glucose into glucose-1-phosphate (G1P) and uridine 5'-monophosphate (UMP).

The present invention also provides an enzyme protein produced by means of recombinant technology (recombinant protein) comprising the amino acid sequence set forth as SEQ ID NO:2 in the Sequence Listing, in a purified form. The recombinant protein have been confirmed to have the UGPPase activity.

The present invention further provides a method for producing a recombinant enzyme protein comprising the steps of: incorporating the DNA comprising the nucleotide sequence set forth as SEQ ID NO:1 in the Sequence Listing into an expression vector, introducing thus constructed expression vector into competent cells, culturing the cells transformed with the constructed expression vector and purifying the expressed protein, wherein the protein has an activity of hydrolyzing UDP-glucose into glucose-1-phosphate and uridine 5'-monophosphate.

The present invention further provides use of the recombinant enzyme protein as a reference standard in the assay of UGPPase activity in samples, wherein the protein comprises the amino acid sequence set forth as SEQ ID NO: 2, wherein the protein has an activity of hydrolyzing UDP-glucose into glucose-1-phosphate and uridine 5'-monophosphate. Such use allows to obtain standardized data of the activity levels of the enzyme, which enables exactly quantitative comparison among the data taken from different samples measured at different times and places.

In addition, the present invention provides a method for preparing purified mammalian UGPPase comprising the steps of:

(a) homogenizing tissue from a mammalian animal in an aqueous medium, (b) centrifuging thus obtained homogenate, (c) collecting the supernatant of the centrifuged homogenate, (d) dialyzing the collected supernatant against an aqueous medium, (e) applying the dialyzed supernatant obtained in (d) above to one or more processes of chromatography using one or more stationary-phase materials, respectively, and collecting fractions exhibiting concentrated UGPPase activity, wherein the stationary-phase material or materials include one selected from the group consisting of anion exchanger, weak anion exchanger, gel for size exclusion, and hydroxyapatite, (f) applying the fractions exhibiting concentrated UGPPase active obtained in (e) above to native PAGE, and (g) cutting out from the gel a portion containing a concentrated UGPPase specific activity and extracting UGPPase protein from the portion of the gel with an aqueous extraction medium.

The method above is more preferably carried out in the presence of one or more sulfhydryl group-protective agents dissolved in the medium used in one or more, and most preferably all, of the steps (d)-(i).

Furthermore, the present invention provides a purified antibody to UGPPase, which antibody may be a polyclonal or monoclonal.

Furthermore, the present invention also provides a method for determining the amount of UGPPase in an analyte based on enzyme-linked immunosorbent assay (ELISA) comprising the steps of:

(a) providing a solid phase onto which an anti-UGPPase antibody is bound, (b) contacting a first solution containing a predetermined amount of the analyte to the solid phase for a length of time sufficient to allow UGPPase contained in the analyte to bind to the anti-UGPPase bound onto the solid phase, (c) after removal of the first, contacting a second solution containing a predetermined amount of an enzyme-conjugated anti-UGPPase antibody to the solid phase for a length of time sufficient to allow the enzyme-conjugated anti-UGPPase antibody to bind to the UGPPase bound to the anti-UGPPase bound to the solid phase, (d) after removal of the second solution, contacting a third solution containing a predetermined amount of an substrate for the conjugated enzyme to the solid phase, and allowing the conjugated enzyme to react with the substrate for a predetermined length of time to produce a specific product of the enzyme reaction, (e) measuring the amount of the thus-produced specific product, and (f) determining the amount of UGPPase in the analyte based on the comparison between the amount of the specific product in (e) and the amount of the specific product produced from predetermined amount of UGPPase under the same conditions as in (b)-(d).

Still further, the present invention also provides a method for determination of the amount of UDPG contained in a given sample, preferably in liquid sample, and more preferably in a biological sample such as blood. As UDPG deficiency occurs in tissues of diabetic animals (patients) (25-27), determination of UDPG in samples will be utilized for identification of diabetic patients. The method, which is based on one-to-one conversion of UDPG to G1P, comprises the steps of:

(a) mixing a predetermined quantity of a sample with a buffer solution containing a predetermined amount of UGPPase to prepare a reaction mixture, (b) incubating the reaction mixture for a sufficient length of time to convert UDPG to G1P, (c) terminating the reaction by heating the reaction mixture, and (d) measuring the amount of G1P produced in (d) by reacting G1P contained at least a known portion of the reaction mixture with phosphoglucomutase, G6P dehydrogenase and NAD, and measuring the amount of NADH produced, e.g., spectrophotometrically at 340 nm.

This method allows to measure the amount of UDPG in human tissues, in which UDPG levels ranges between 0.1 mM and 1 mM in non-diabetic humans (28, 29).

BRIEF DESCRIPTION OF DRAWINGS

FIG. 6 shows the first half of the results of ESI-TOF MS/MS. The first half of the deduced amino acid sequences of AAD15563.1 (human) and BAB23110.1 (mouse) are lined with the amino acid sequences of porcine UGPPase fragments. Amino acids common to the species are marked with " • • • ", while those only common to pig and one of human or mouse are marked with "•".

FIG. 7 shows the second half of the results of ESI-TOF MS/MS. The second half of the deduced amino acid sequences AAD15563.1 (human) and BAB23110.1 (mouse) are lined with the amino acid sequences of porcine UGPPase fragments. Amino acids common to the species are marked with " • • • ", while those only common to pig and one of human or mouse are marked with "•".

BEST MODE FOR CARRYING OUT THE INVENTION

Figure 1:
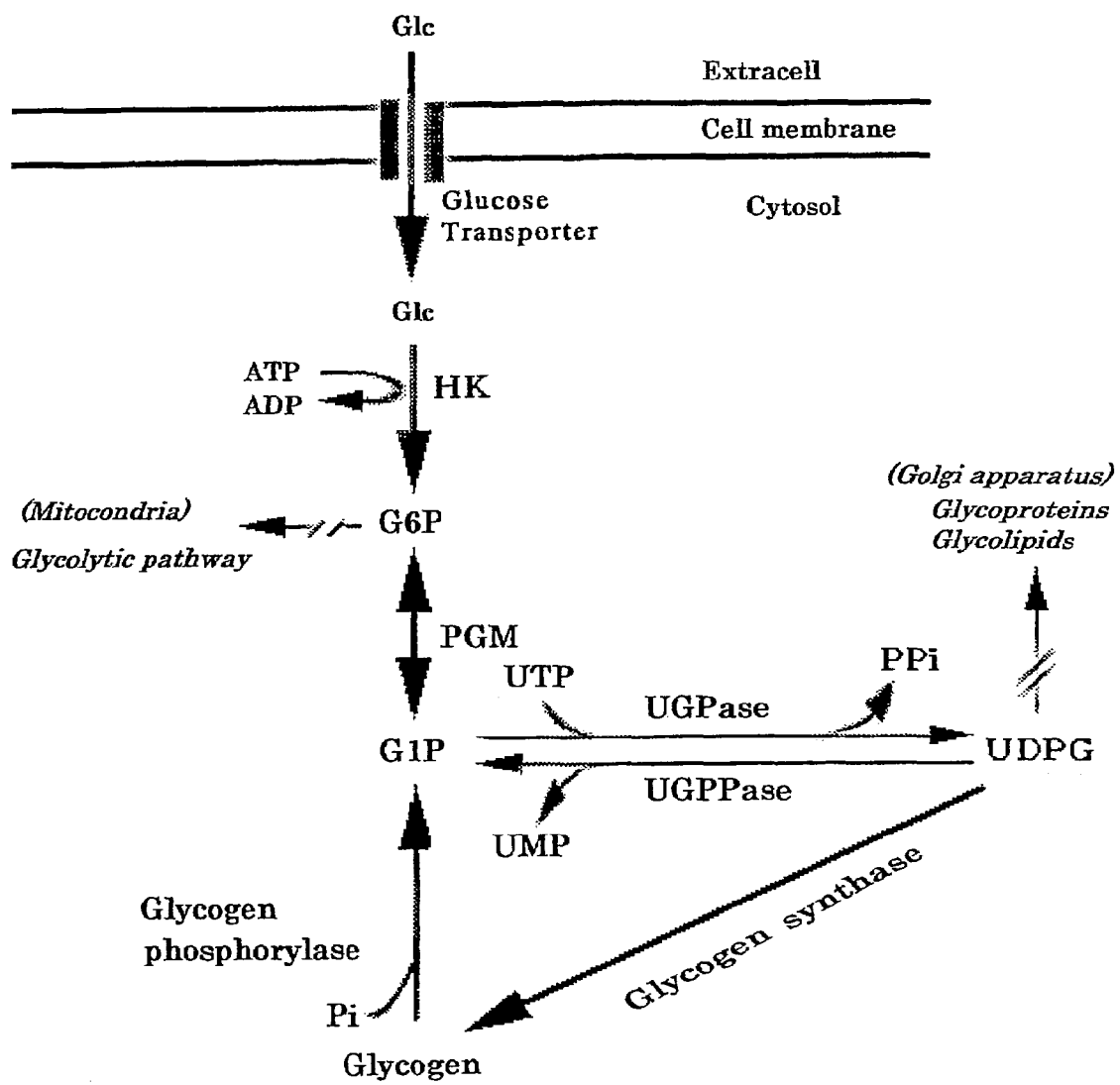
FIG. 1 illustrates a schematic flow of biochemical reactions in animal cells relating to glycogen metabolism, in which UGPPase is considered to be taking part. In the figure: Glc; glucose, HK; hexokinase, PGM; phosphoglucomutase.

The present invention will be described in further detail below with reference to the processes for, and the results of, isolation and purification of porcine UGPPase, production of human recombinant UGPPase, their enzymatic characterization, production of an anti-UGPPase antibody, measurement of UGPPase based on ELISA. and determination of UDP-glucose contained in a sample.

An anti-UGPPase monoclonal antibody can also be produced by a conventional method for preparing a monoclonal antibody, which comprises such steps as inoculation of animals (e.g., mice) with UGPPase, removal of the spleen of an animal showing sufficient antibody titers, B cell selection, fusion of the B cells with myeloma cells of B cell origin to form hybridoma cells secreting the antibody, and purification of the antibody from the culture medium. A polyclonal antibody may be produced using any mammalian animals such as rabbits, horses, mice and guinea pigs.

EXAMPLES

Materials and Methods:

(1) Methods for Measurement of UGPPase Activity

UGPPase activity is defined based on the amount of G1P produced by the enzyme. The measurement is carried in two-step reactions according to the method reported by Rodriguez-Lopez et al. (11). In the first reaction, 50 μl of the reaction mixture consisting of a sample containing UGP-Pase, 0-20 mM concentration of a sugar nucleotide (UDP-, ADP- or GDP-glucose)(SIGMA), 20 mM MgCl$_2$, and 50 mM Tris-HCl (pH 9.0), and the mixture is incubated at 37° C. for 30 minutes. As a blank, the same sample that has been boiled for two minutes to inactivate UGPPase is used. After the incubation period, the reaction is terminated by a two-minute boiling, and the mixture centrifuged at 20,000 g for 10 minutes at 4° C.

The second reaction is carried out in a 300-μl reaction mixture consisting of 50 mM HEPES (pH 7.5), 1 mM EDTA, 2 mM MgCl$_2$, 15 mM KCl, 1 unit phosphoglucomutase (ROCHE), 0.6 mM NAD (SIGMA), 1 unit glucose-6-phosphate dehydrogenase (SIGMA), and 30 μl of the supernatant of the first reaction. The reaction mixture is placed in a 96-well FluoroNunc™ plate (NUNC) and incubated at 37° C. for 10 minutes. This second reaction produces an equimolar amount of NADH to that of G1P produced in the first reaction. The amount of NADH is determined by measuring OD at 340 nm using a microplate reader (MOLECULAR DEVICE).

The amount (activity) of UGPPase contained in a sample is expressed in unit (U), in which one unit is defined as the strength of the enzyme activity that hydrolyzes one pmol of UDPG a minute. The activity was calculated as follows:

$$1U=[a]/30/0.03$$

where [a] is the amount in μmol of NADH produced in the reaction.

The above conditions of the first reaction were modified according to the purpose of each of the test, as specifically indicated below.

(2) Extraction of Porcine UGPPase:

Fresh porcine kidney, 3.6-kg of weight, was homogenized in 12 liters of a 50 mM HEPES buffer (pH 7.0) containing 2 mM DTT and 2 mM EDTA (0.3 g tissue per 1 ml buffer) and filtered through Miracloth™ (CALBIOCHEM). After centrifugation at 30,000 g for 30 minutes at 4° C., two-liter portion of the supernatant was dialyzed for 12 hours against 20 liters of dialysate solution (1 mM DTT, 1 mM 2-mercaptoethanol) at 4° C. using a dialyzer membrane (MW 14 kDa cut), and for further 12 hours against the same volume of the fresh dialysate solution. This procedure was repeated (5 times in total) to treat the whole volume of the supernatant. All the buffer used hereafter contained 1 mM DTT and 1 mM 2-mercaptoethanol. After centrifugation at 100,000 g for 30 minutes at 4° C., Tris-HCl was added to the supernatant up to the final concentration of 50 mM (pH 8.0). Three liters of this sample were taken and mixed well with 2 liters of Q Sepharose Fast Flow resin (AMERSHAM PHARMACIA BIOTECH), and filtrate then was removed through a glass filter. Proteins bound to the resin were eluted successively with two liters each of the buffer containing 50 mM Tris-HCl (pH 8.0) and NaCl at 0, 0.1, 0.2, 0.3, 0.4 or 0.5 M, respectively, in the order. The procedures were followed four times to treat the whole volume of the sample. UGP-Pase-active eluate fractions were collected and combined.

A half (six liters) of the active eluate obtained above were dialyzed for 12 hours against 20 liters of the dialysate solution (1 mM DTT, 1 mM 2-mercaptoethanol, 50 mM Tris-HCl, pH 8.0) at 4° C., and for further 12 hours against the same volume of the fresh dialysate solution. Twelve liters of this buffer-exchanged solution were mixed well with one liter of Q Sepharose Fast Flow resin (AMERSHAM PHARMACIA BIOTECH), and filtrate then was removed through a glass filter. Proteins bound to the resin were eluted successively with one liter each of the buffer containing 50 mM Tris-HCl (pH 8.0) and NaCl at 0, 0.1, 0.2, 0.3, 0.4 or 0.5 M, respectively, in the order. The procedures were followed twice to treat the whole volume of the sample.

Combined UGPPase-active fractions, which made up to 1.6 liters of volume, were dialyzed against 20 liters of the dialysate solution (1 mM DTT, 1 mM 2-mercaptoethanol) at 4° C. for 12 hours. After addition of sodium hydrogen phosphate buffer (pH 7.0) at the final concentration of 1 mM, the dialyzed solution was mixed well with 100 g of hydroxyapatite resin (SEIKAGAKU CORPORATION) that had been equilibrated with the same buffer. After removal of filtrate through a glass filter and washing with 200 ml of 1 mM sodium hydrogen phosphate buffer (pH 7.0), proteins adsorbed to the hydroxyapatite resin were eluted with 200 ml of 400 mM sodium hydrogen phosphate buffer (pH 7.0). UGPPase-active fractions from the hydroxyapatite resin were combined and buffer exchanged for 40 mM Tris-HCl (pH 8.0). Six hundred ml of this solution at a time was loaded onto a Q Sepharose HP HiLoad 26/10 column (AMERSHAM PHARMACIA BIOTECH) and eluted with 500 ml of 40 mM Tris-HCl (pH 8.0) with a 0-0.5 M NaCl linear gradient at a flow rate of 5 ml/min. This procedure was followed total three times to treat the whole volume of the solution. Fifteen ml of combined UGPPase-active fractions at a time was loaded onto a Superdex 200 column (AMERSHAM PHARMACIA BIOTECH) that had been equilibrated with 500 ml of 50 mM HEPES buffer (pH 7.5) containing 0.2 M NaCl. The column was eluted with the same buffer at a flow rate of 3 ml/min for molecular weight fractionation. These procedures were followed eight times in total to treat the whole volume of the combined UGPPase-active fractions.

Active fractions were combined and dialyzed against 10 liters of the dialysate solution (1 mM DTT, 1 mM 2-mercaptoethanol, 50 mM Tris-HCl, pH 8.0) at 4° C. for 12 hours. This solution, 85 ml at a time, was loaded onto a MonoQ HR5/5 column (anion exchanger, AMERSHAM PHARMACIA BIOTECH) that had been equilibrated with 50 mM Tris-HCl (pH 8.0), and the column was eluted with 30 ml of 40 mM Tris-HCl (pH 8.0) with a 0-0.5 M NaCl linear gradient at a flow rate of 1 ml/min. This procedure was followed three times to treat the whole volume of the solution.

Active fractions collected and combined were dialyzed against five liters of the dialysate solution (1 mM DTT, 1 mM 2-mercaptoethanol, 75 mM Tris-HCl, pH 9.0) at 4° C. for 12 hours. Eleven ml at a time of this dialyzed solution was loaded onto a MonoP HR5/20 (weak anion exchanger, AMERSHAM PHARMACIA BIOTECH) column that had been equilibrated with 75 mM Tris-HCl (pH 9.0), and the column was eluted with 40 ml of 50 mM Tris-HCl (pH 9.0) with a 0-0.5 M linear NaCl gradient at a flow rate of 1 ml/min. This procedure was followed twice to treat the whole volume of the dialyzed solution.

Active fractions was dialyzed against one liter of the dialysate solution (1 mM DTT, 1 mM 2-mercaptoethanol) at 4° C. for 12 hours, and lyophilized to reduce the volume of the solution from three ml to two ml. To this was added 500 μl of x5 native PAGE sample treatment solution (312.5 mM Tris-HCl, pH 7.8, 75% glycerol, 0.005% BPB). Then, 500 μl each of this sample was applied to a sheet of 12.5% polyacrylamide gel (five sheets in total). The gel was subjected to electrophoresis using a buffer containing 0.025 M Tris and 0.192 M glycine (pH 8.4) at 40 mA for two hours (23). After completion of the electrophoresis, the gel was cut into pieces at 3-mm interval in the longitudinal direction of the gel. Each cut out pieces of the gel was separately suspended in a 500 μl of an extraction buffer (10 mM Tris, pH 7.4, 10 mM 2-mercaptoethanol, 500 mM NaCl) and allowed to stand for 12 hours at 4° C. to extract proteins. Protein fractions from those cut out pieces that were confirmed to exhibit UGPPase activity and to give a single band on SDS-PAGE were collected as the final, purified UGPPase product.

(3) Molecular Weight Analysis:

The purified porcine UGPPase was subjected to SDS-PAGE (10-20% acrylamide gradient gel). Bands stained with Coomassie Brilliants Blue (CBB) were excised from the gel and freeze-dried. The protein was extracted from the gel and digested with trypsin at 37° C. for 16 hours into peptide fragments, which were purified, desalted and concentrated using ZipTip (MILLIPORE) and subjected to mass spectrometry on Micromass Q-TOF MS (MICROMASS). In the mass spectrometer, peptide fragments were ionized by ESI (electrospray ionization) method, and thus produced peptide ions were separated according to their Mass-to-charge ratio (m/z). Peptide ions having their m/z of 400-1800 were selected and further fragmented by collision energy with rare gas molecules to generate ion ladders having m/z of 50-2000. Two types of ladders were obtained, one series consisting of fragments from the N-terminus and another from the C-terminus. Mass differences between fragments were determined in a TOF (time of flight) mass spectrometry system and information on amino acid sequence either from N- or C-terminus of the protein was obtained.

Figure 8:
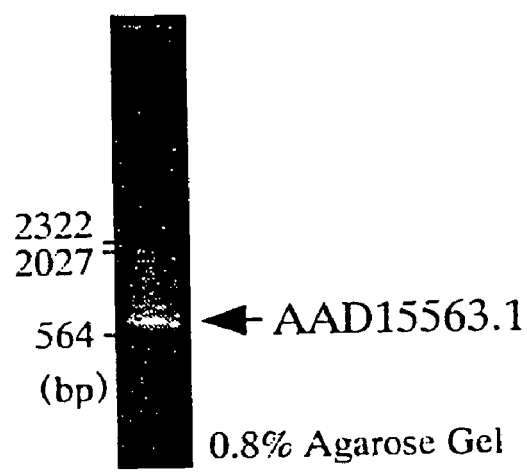
FIG. 8 shows the result of the electrophoresis (0.8% agarose gel) of the PCR amplification product.
Figure 9:
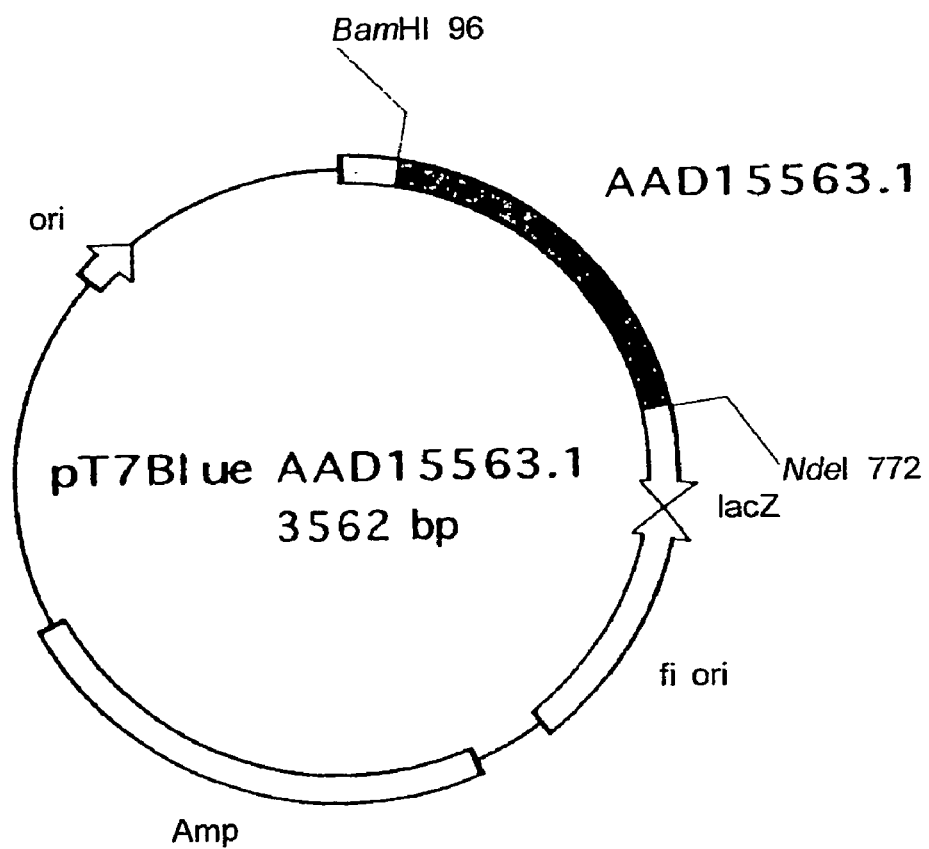
FIG. 9 illustrates a pT7Blue T-vector with incorporated AAD15563.1.

(4) PCR Cloning of AAD15563.1 cDNA:

PCR was performed to amplify AAD15563.1 cDNA, using 1.6 μg of cDNA library from human thyroid grand, 4 pmol of a forward primer 5'-CATATGGAGCGCATC-GAGGGGGCGTCCGT-3' (SEQ ID NO:9), which included at its 5' end an NdeI cleavage site, 4 pmol of a reverse primer 5'-GGATCCTCACTGGAGATC CAGGTTGGGGGCCA-3' (SEQ ID NO:10), which included a BamHI cleavage site, 1 unit of AmpliTaq Gold (PERKIN ELMER) DNA polymerase and 0.2 mM dNTP (PERKIN ELMER) in AmpliTaq Gold Buffer (PERKIN ELMER), in the final volume of 20 μl, on Gene Amp PCR System 9700 (PERKIN ELMER), under the following conditions: 94° C. for 5 min; 35 cycles of (94° C. for 1 min, 55° C. for 1.5 min and 72° C. for 2 min); 72° C. for 5 min; and then 4° C. Electrophoresis (0.8% agarose gel) of the reaction product showed a single band of AAD15563.1 (FIG. 8.) Fifty ng of thus amplified 678 bp cDNA fragment was purified with GFX™ PCR DNA and Gel Band Purification kit (a kit including a chaotropic agent-containing buffer to denature protein and dissolve agarose, a micro column pre-packed with glass fiber matrix to specifically adsorb DNA, a Tris-EDTA wash buffer, and autoclaved double-distilled water for elution: AMERSHAM PHARMACIA BIOTECH), mixed with 25 μg of pT7Blue T-vector (NOVAGEN) DNA and the volume of the solution was adjusted to 5 µl with distilled water. This was then mixed with 5 µl of Solution I (a T4 DNA ligase-containing buffer) of Ligation Kit Ver.2 (TAKARA) and left stand at 16° C. overnight to clone the cDNA fragment into the vector (FIG. 9). The vector carrying the cDNA was introduced into E. coli (JM109) and the cells were left stand at 37° C. overnight in LB 1.5% agar medium (GIBCO BRL). Some of the single colonies formed on the agar medium were cultured in 2 ml of LB liquid medium containing 50 µg/ml ampicillin (LB+Amp)(DIFCO) at 37° C. overnight with stirring. The culture was centrifuged at 18,000 g for five minutes at 4° C., and the supernatant was discarded. Plasmids were extracted from the precipitated cells using RPM™ kit (BIO 101, INC.). 500 ng of plasmid chosen from some of the clones was reacted, respectively, with 1 unit each of the restriction enzymes NdeI (TAKARA) and BamHI (TAKARA) in K buffer (20 mM Tris-HCl, pH 8.5, 10 mM $MgCl_2$, 1 mM dithiothreitol, 100 mM NaCl) (TAKARA), in the final volume of 15 µl and at 37° C. for one hour. After the reaction, the reaction mixture was subjected to electrophoresis in 0.8% agarose gel. The plasmid clones were examined and those carrying the cDNA were selected.

(5) Confirmation of the Sequence of the Inserted AAD15563.1 cDNA:

Some of the plasmids selected above were used for confirmation of the nucleotide sequence of inserted AAD15563.1 cDNA. Twelve µl of the reaction mixture contained 400 ng of one of the plasmids, 2 pmol of T7 primer (T7 promoter primer: 5'-TCTAATACGACTCAC-TATAGG-3') (SEQ ID NO:11), 2 pmol of M13 primer M4 (5'-GTTTTCCCAGTCACGAC-3') (SEQ ID NO:12), 4.8 µl of the reaction solution attached to the Dye Terminator Ready Reaction Kit (ABI). Sequencing reaction was carried out on Gene Amp PCR System 9700 (PERKIN ELMER), under the following conditions: (96° C. for 10 sec, 50° C. for 5 sec, and 60° C. for 4 min)×25 cycles and 4° C. 1.2 µl of 3M sodium acetate and 30 µl of 100% ethanol were added to the total volume of the reaction mixture to give a suspension. The suspension then was left stand for 20 min on ice and centrifuged at 18,000 g for 20 minutes. The supernatant was discarded, and 200 µl of 70% ethanol was added to suspend the precipitate, which then was centrifuged at 18,000 g for 5 minutes. The supernatant was discarded, and the precipitate was dried, resuspended in 10 µl of Template Suppression Reagent (PERKIN ELMER), left stand at 95° C. for 2 minutes, and cooled quickly on ice for 2 minutes. This sample was analyzed on ABI PRISM310 Genetic Analyzer (PERKIN ELMER) to determine the nucleotide sequence of the cDNA inserted in the plasmid. After having determined the nucleotide sequences from several clones, a clone carrying the DNA having the same sequence as that reported for AAD15563.1 cDNA was selected.

Figure 10:
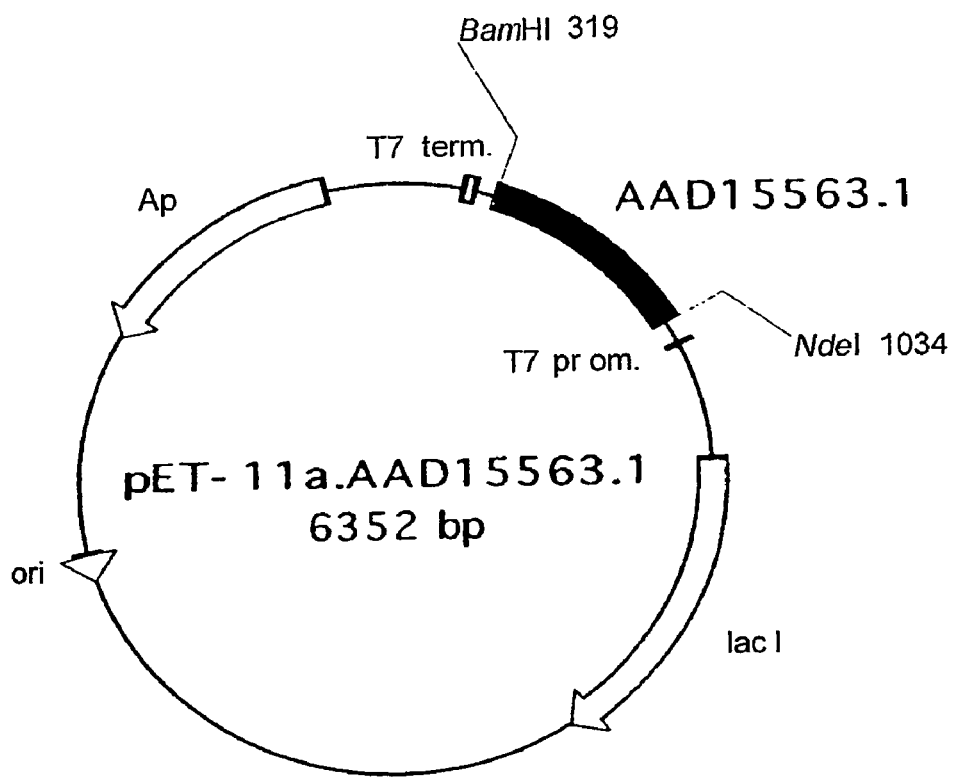
FIG. 10 illustrates a pET11a with incorporated AAD15563.1.
Figure 11:
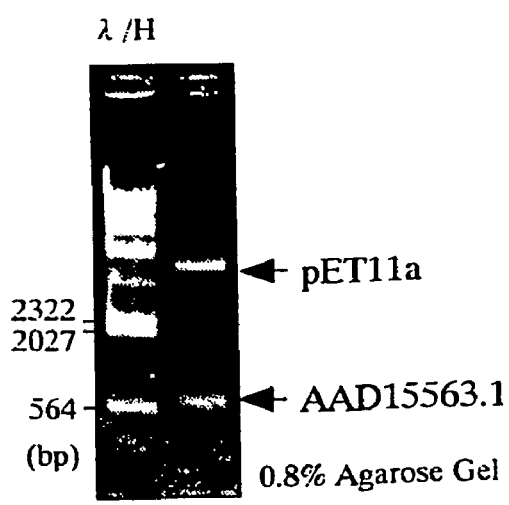
FIG. 11 shows the result of the electrophoresis (0.8% agarose) of the NdeI/BamHI-digested pET11a.AAD15563.1.

(6) Insertion of AAD15563.1 cDNA into an Expression Vector:

One µg of the plasmid clone that had been confirmed to have the DNA of interest was digested with restriction enzymes, NdeI and BamHI (both from TAKARA). Separately, pET11a vector (NOVAGEN) was digested with the same restriction enzymes. The digested plasmid and the vector were subjected to electrophoresis, respectively, in 0.8% agarose gel. After staining with 1 µg/ml of ethidium bromide, the bands corresponding to the cDNA fragment and pET11a, respectively, were cut out from the gel, and extracted and purified using GFX™ PCR DNA and Gel Band Purification kit (AMERSHAM PHARMACIA BIO-TECH). Using 50 ng of the purified cDNA fragment and 25 ng of pET11a, the fragment was ligated to the expression vector for re-cloning in the same manner as described above with regard to ligation of the 678-bp cDNA fragment and pT7Blue T-vector DNA. The obtained plasmid (FIG. 10) was introduced into E. coli (JM109) cells and then recovered from the cells as described above. The recovered plasmid was confirmed to have AAD15563.1 DNA by NdeI/BamHI digestion followed by agarose gel electrophoresis (FIG. 11). The plasmid then was introduced into E. coli AD494(DE3) (NOVAGEN), a host adapted for high expression of foreign proteins. Thus obtained transformant was deposited as of on Feb. 12, 2002 with IPOD International Patent Organism Depository, of AIST Tsukuba Central 6, 1-1, Higashi 1-chome, Tsukuba-shi, Ibaraki-Ken 305-8566 Japan (Accession No. FERM BP-7886).

(7) Expression and Purification of Recombinant AAD15563.1 Protein:

The E. coli AD494(DE3) cells transformed above with the plasmid pET11a-AAD15563.1 were cultured in 10 ml of LB liquid medium containing 50 µg/ml ampicillin (LB+Amp)(DIFCO) at 37° C. overnight with stirring. The entire cells then were inoculated into one liter of fresh LB+Amp medium contained in a five-liter Erlenmeyer flask and cultured at 37° C. When $OD_{550}$ of the culture reached about 0.5, 1 mM isopropyl-β-D-thiogalactopyranoside was added to the medium, and the culture was continued for further 3 hours at 37° C. The culture was centrifuged at 8,000 g for 15 minutes at 4° C. The supernatant was discarded, and precipitated cells were collected, suspended in 100 ml of 50 mM Tris-HCl (pH 8.5), and centrifuged at 10,000 g for 15 minutes at 4° C. The supernatant was discarded, and the precipitated cells were suspended in 100 ml of 50 mM Tris-HCl (pH 8.5) containing 1 mM DTT and 1 mM 2-mercaptoethanol, and lysed by sonication on ice. After centrifugation at 10,000 g for 15 min at 4° C., the supernatant was recovered, filtered through a membrane with the pore size of 0.45 µm and loaded onto a Q Sepharose HP HiLoad 26/10 column (AMERSHAM PHARMACIA) that had been equilibrated with 50 mM Tris-HCl (pH 8.5) containing 1 mM DTT and 1 mM 2-mercaptoethanol. After washing with 100 ml of the equilibration buffer, the column was eluted with 500 ml of the equilibration buffer with a 0-1.5 M NaCl linear gradient at a flow rate of 5 ml/min. UGPPase-active fraction (18 ml) was collected and dialyzed overnight against one liter of a dialysate solution consisting of 1 mM DTT and 1 mM 2-mercaptoethanol. This dialyzed active fraction was buffer exchanged for 50 mM Tris-HCl (pH 8.5). This fraction then was loaded onto a MonoP HR5/20 column that had been equilibrated with 20 ml of 50 mM Tris-HCl (pH 8.5) containing 1 mM DTT and 1 mM 2-mercaptoethanol. The column was eluted with 40 ml of this equilibration buffer with a 0-1.5 M NaCl linear gradient at a flow rate of 1 ml/min. The fraction that exhibited the highest UGPPase activity and the highest purity was selected as the final purified product.

(8) Northern Blot Analysis of Normal Tissues from Pig and Human Adult

Northern blot analysis was carried out using total RNA from different normal tissues of pig and human in order to examine expression levels of UGPPase in those tissues. Pig tissues examined were those from the muscle, heart, liver, kidney, lung, brain and fat tissue. For human Northern blot, a commercially available premade Northern blot (Human Adult Normal Tissue Total RNA Northern Blot I, Catalog No. 021001: BIOCHAIN INSTITUTE, INC, Hayward, Calif.) was used, which contained total RNA from eight different human normal tissues (heart, brain, kidney, liver, lung, pancreas, spleen and skeletal muscle) that had been run on denaturing formaldehyde 1% agarose gel and transferred to a charged-modified nylon membrane.

(9) Preparation of Anti-hUGPPase Antibody

The final purified product of hUGPPase obtained in (7) above was used as the antigen to produce an anti-hUGPPase antibody. Two hundred µg of the antigen protein was placed in an 1.5-ml Eppendorf tube and 1 ml of GERBU™ ADJUVANT 100 (including 0.025 mg/L glycopeptide derived from *L. bulgaricus* cell walls, 50 g/L paraffin based nanoparticles, cationizers, cimetidine and saponin: BIOTECH-NIK GmbH) was added (Alternatively, Freund's complete adjuvant may be employed). The mixture was stirred by a vortex mixer for 30 min at room temperature to obtain an antigen emulsion. One 10-week old New Zealand white rabbit was immunized by injecting the animal with this antigen emulsion into a muscle of a hind limb once in every other week. Five weeks after the start of the immunization procedure, the animal was sacrificed and the antiserum was prepared by a conventional method. The antiserum (anti-hUGPPase antiserum) was divided into two tubes and stored at 4° C. and −20° C., respectively.

(10) Recombination of AAD15563.1 cDNA into His-tag Fusion Protein Expression Vector pET-19b One µg of pET-11a AAD15563.1, whose nucleotide sequence had been confirmed, was digested with restriction enzymes, NdeI and BamHI, in the order. Separately, pET-19b vector (NOVAGEN) was digested with the same restriction enzymes in the order. The respective reaction mixtures were subjected to 0.8% agarose electrophoresis and, after staining with 1 µg/ml ethidium bromide and under ultraviolet illumination, bands corresponding to hUGPPase cDNA and pET-19b vector were cut out from the gel. The DNA fractions were extracted from the gel using GFX™ PCR DNA and Gel Band Purification Kit (AMERSHAM BIO-SCIENCES) and purified. Fifty ng of the hUGPPase cDNA fragment then was mixed with about 25 ng of the pET-19b vector, and 5 µl of Solution I of Ligation Kit Ver.2 (TAKARA) was to the mixture added, and ligation reaction was allowed to take place at 16° C. overnight. Thus constructed plasmid pET-19b AAD15563.1 was introduced into *E. coli* AD494(DE3) cells.

(11) Expression and Purification of hUGPPase His-tag Fusion Protein

The *E. coli* AD494(DE3) cells harboring plasmid pET-19b AAD15563.1 were shake-cultured in LB+Amp liquid medium [Miller's LB Broth Base (GIBCO BRL), 50 µg/ml ampicillin sodium salt] at 37° C. overnight. On the following day, all the cells were transferred to 1 L of LB+Amp liquid medium in a 5-L Erlenmeyer flask. The cells were shake-cultured at 37° C., and when OD at 600 nm of the culture reached about 0.5, isopropyl-β-D-thiogalactopyranoside was added to the medium at the final concentration of 1 mM, and shake-culture was continued for further 3 hours at 37° C. The culture then was centrifuged at 8,000 g for 15 minutes at 4° C. Precipitated cells were resuspended in 250 ml of 50 mM Tris-HCl, 1 mM 2-mercaptoethanol, 0.1% Triton X-100, pH 9.0. The cells were sonicated on ice, centrifuged at 10,000 g for 15 min at 4° C., and the supernatant was collected. The procedure was repeated on 6 L of the *E. coli* culture medium to obtain 1.3 L of supernatant in total. The supernatant was filtered through a membrane filter with a pore size of 0.45 µm and the whole volume of it was loaded onto a Q Sepharose HP HiLoad 26/10 column (AMERSHAM BIOSCIENCES) that had been equilibrated with 50 mM Tris-HCl, 1 mM 2-mercaptoethanol, 0.1% Triton X-100, pH 9.0. The column was washed with 100 ml of the equilibration buffer and the adsorbed protein then was eluted with 500 ml of this equilibration buffer with a 0-1.5 M NaCl linear gradient at a flow rate of 5 ml/min. A UGPPase-active fraction (60 ml) was collected and the whole volume of it was loaded onto a 5-ml TALON™ metal affinity resin (Co-immobilized affinity resin: CLONTECH) that had been equilibrated with 50 mM Tris-HCl, 1 mM 2-mercaptoethanol, 0.1% Triton X-100, pH 9.0. The column was washed with 20 ml of this equilibration buffer spiked with 10 mM imidazole and then eluted with the equilibration buffer spiked with 150 mM imidazole to collect a UGPPase-active fraction (13.5 ml). This fraction then was loaded onto a Superdex™-200 HR column (gel filtration column consisting of highly cross-linked porous agarose beads carrying covalently bound dextran: AMERSHAM PHARMACIA BIOTECH) that had been equilibrated with 0.2 M NaHCO$_3$, 0.1 M NaCl, pH 8.3 and gel-filtered at a flow rate of 5 ml/min. The most UGPPase-active and most purified fraction was collected as the final, purified hUGPPase His-tag fusion protein product.

(12) Western Blot Analysis of hUGPPase His-Tag Fusion Protein

To insure that the final, purified product obtained above is hUGPPase His-tag fusion protein, Western blot analysis was carried out using the anti-hUGPPase antiserum obtained in (9) above and a commercially available anti-histidine tag monoclonal antibody (SIGMA). One µg of the hUGPPase His-tag fusion protein was separated by SDS-PAGE (10-20% acrylamide gradient gel (DAIICHI PURE CHEMICALS CO., LTD.), and transferred to Trans-blot Transfer Membrane (BIO-RAD) at 4° C. at 100 V for 2 hours. The membrane was blocked with 3% (w/v) skim milk in TBS [Tris-buffered saline, pH 8.0 (SIGMA)], and reacted with an anti-His tag mouse monoclonal antibody (GENZYME/TECHNE) diluted to 500 ng/ml with TTBS [Tris buffered saline with 0.05% Tween 20, pH 8.0 (SIGMA)] and then with the anti-hUGPPase antiserum that was diluted 1,000 folds with TTBS, respectively for 1 hour at room temperature. The membrane was washed with TTBS 3 times, for 5 min each. The membrane was incubated at 37° C. for 1 hour either with an alkaline phosphatase-conjugated goat anti-mouse IgG (BIO-RAD) diluted 1000 folds with TTBS for detection based on the anti-His tag monoclonal antibody, or an alkaline phosphatase-conjugated goat anti-rabbit IgG (BIO-RAD) diluted 1,000 folds with TTBS for detection based on the anti-hUGPPase antiserum. After the membrane was washed with TTBS 3 times, for 5 min each, a substrate solution was added to the membrane to allow for color development.

(13) Preparation of Antigen Column

For affinity purification of the anti-hUGPPase antibody from the rabbit anti-hUGPPase antiserum, the inventors attempted preparation of an antigen column based on hUGPPase His-tag fusion protein. Eight mg of purified hUGPPase His-tag fusion protein was prepared in 14.3 ml of 0.2 M NaHCO$_3$, 0.5 M NaCl, pH 8.3. This was loaded onto a 5-ml HiTrap NHS-activated column (N-hydroxysuccinimide-activated Sepharose®: PHARMACIA BIOTECH) that had been equilibrated with 1 mM HCl to allow the protein to covalently bind to the column. The column was then washed with 30 ml of 1 M Tris-HCl, 0.5 M NaCl, pH 8.3 and 30 ml of 0.1 M citrate, 0.5 M NaCl, pH 3.0, in the order.

(14) Purification of Anti-hUGPPase Antibody

After the antigen column prepared above was equilibrated with PBS, 20 ml of the anti-hUGPPase antiserum was applied to the column. The column was washed with 20 ml of PBS and then eluted with 0.1 M citrate, 0.5 M NaCl, pH 3.0. Fractions were neutralized with 1 M Tris-HCl, pH 9.5. Antibody fraction (15.8 ml) was dialyzed overnight against 5 L of distilled water, and then lyophilized.

(15) Labeling of Rabbit Anti-hUGPPase Antibody

The rabbit anti-hUGPPase antibody obtained above was dissolved in 100 mM NaHCO$_3$, pH 8.3 at the final concentration of 4 mg/ml. To 150 μl of this solution was added 50 μl of Peroxidase, Activated (activated peroxidase from horse radish: ROCHE) and allowed to stand for 2 hours at room temperature to let horseradish peroxidase (HRP) bind to the antibody. After the addition of 20 μl of 1 M Tris-HCl, pH 8.0 and then 25 μl of 200 mM NaBH$_4$, the mixture was kept at 4° C. for 30 min. Then 12.5 μl of 200 mM NaBH$_4$ was added and the mixture was kept at 4° C. for 2 hours to completely terminate the reaction. After addition of 5 μl of 1 M glycine, pH 7.0 for stabilizing the antibody, the solution was dialyzed against 1.5 L of PBS, 10 mM glycine, pH 7.4 at 4° C. overnight. Thus obtained solution of the labeled antibody was stored at 4° C. as the HRP-conjugated rabbit anti-hUGPPase antibody.

(16) hUGPPase ELISA

The rabbit anti-hUGPPase antibody prepared in (14) above was diluted with 50 mM NaHCO$_3$, pH 9.6 to prepare a 25 μg/ml solution. The solution was added to the wells of a 96-well plate (NUNC), 100 μl each, and incubated at 37° C. for 1 hour for coating. The antibody solution was removed and 300 μl of a blocking buffer [1.0% (w/v) BSA, PBS, 10 mM glycine, pH 7.4] was added to each well and incubated at 37° C. for 1 hour for blocking.

For preparation of a standard, hUGPPase His-tag fusion protein was diluted stepwise to 10 μg/ml-0.1 ng/ml using a dilution buffer [20 mM Tris, 150 mM NaCl, 0.1% (w/v) BSA, pH7.4].

To use as samples, two types of *E. coli* AD494(DE3) cells, the one with introduced plasmid pET-19b AAD15563.1 and the other with plasmid pET-19b, respectively, were lysed and diluted to 50, 5, 0.5 and 0.05 μg/ml with the dilution buffer. Each well of the plate was removed of the blocking buffer and washed 3 times with 300 μl each of TTBS. To each well was added 100 μl of the standard or the sample solution and an incubation followed at 37° C. for 1 hour.

For detection of hUGPPase His-tag fusion protein, the HRP-conjugated rabbit anti-hUGPPase antibody prepared in (15) was used after dilution to 0.5 μg/ml with the dilution buffer. After the wells were washed 3 times with TTBS, 100 μl of the detection antibody solution was added to each well and incubated at 37° C. for 1 hour. The wells then were washed 3 times with TTBS, and 100 μl of TMB LIQUID SUBSTRATE SYSTEM FOR ELISA (liquid substrate system for ELISA containing chromogen 3,3'5,5'-tetramethyl-benzidine (TMB) and hydrogen peroxide in a buffer, pH 6.0: SIGMA) to each well. After a 5-min incubation at room temperature, 50 μl of 2M H$_2$SO$_4$ was added to each well to terminate the reaction, and OD at 450 nm was measured.

(17) Determination of UDPG in a Sample

Examination was performed to establish a method for determination of UGPG in a sample. In the method, the amount of UDPG was determined as the amount of G1P produced by UGPPase-catalyzed hydrolytic breakdown of UDPG in the sample.

Figure 25:
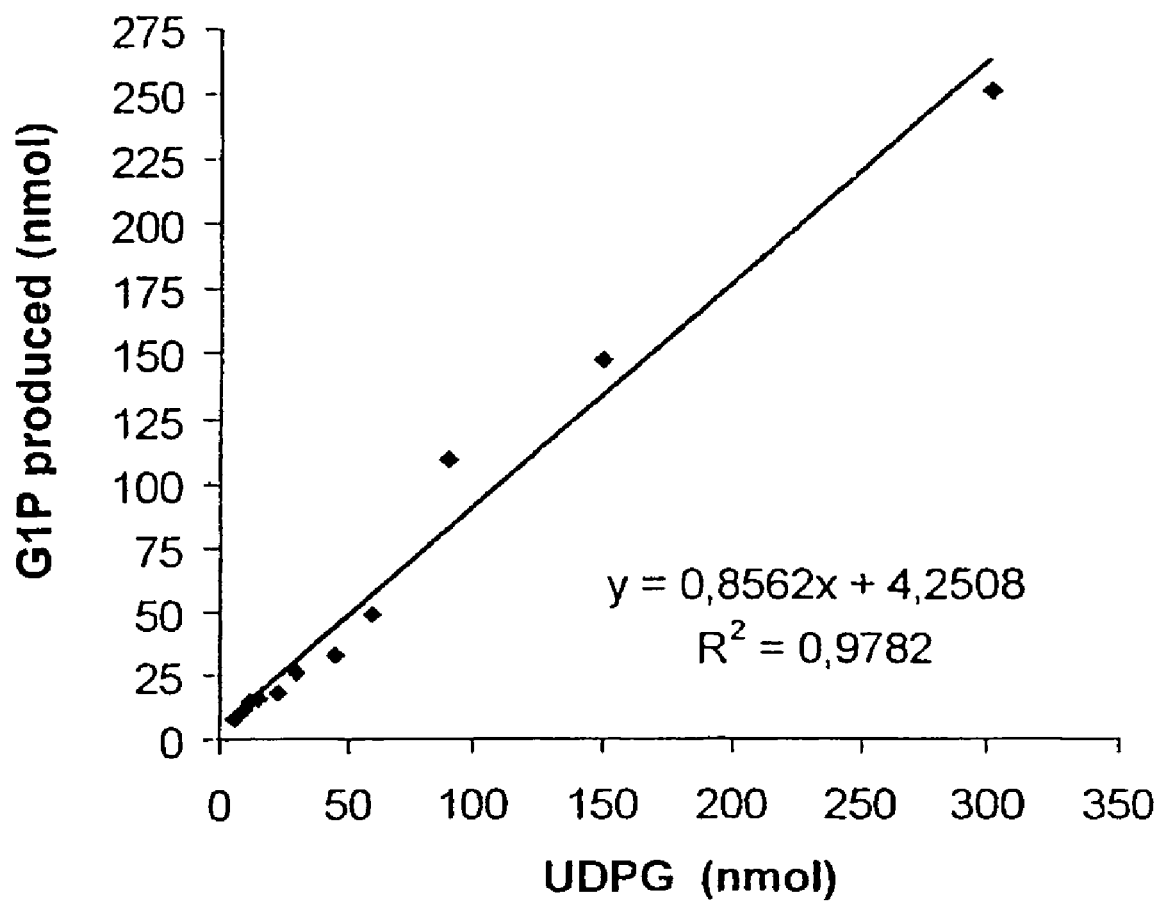
FIG. 25 is a graph showing the correlation between the UDPG amount initially contained in the samples and the G1P amount measured utilizing UGPPase.

Twenty μl of a liquid sample containing UDPG in one of the amounts indicated in FIG. 25 were added to a 30 μl cocktail including 1.5 units of UGPPase, 30 mM MgCl$_2$ and 70 mM Tris-HCl (pH 9.0). After 7 minutes of incubation at 37° C., the reaction was terminated by heating at 100° C. for 2 minutes. The assay mixture was then centrifuged at 20,000×g for 5 minutes. Thirty μl of the supernatant were then added to a 270-μl cocktail containing 50 mM Hepes, pH 7.0, 1 mM EDTA, 2 mM MgCl$_2$, 15 mM KCl, 0.4 mM NAD$^+$, and 3 units each of G6P dehydrogenase and phosphoglucomutase. The amount of NADH (indicating the amount of G1P) produced was then spectrophotometrically measured at 340 nm.

Figure 2:
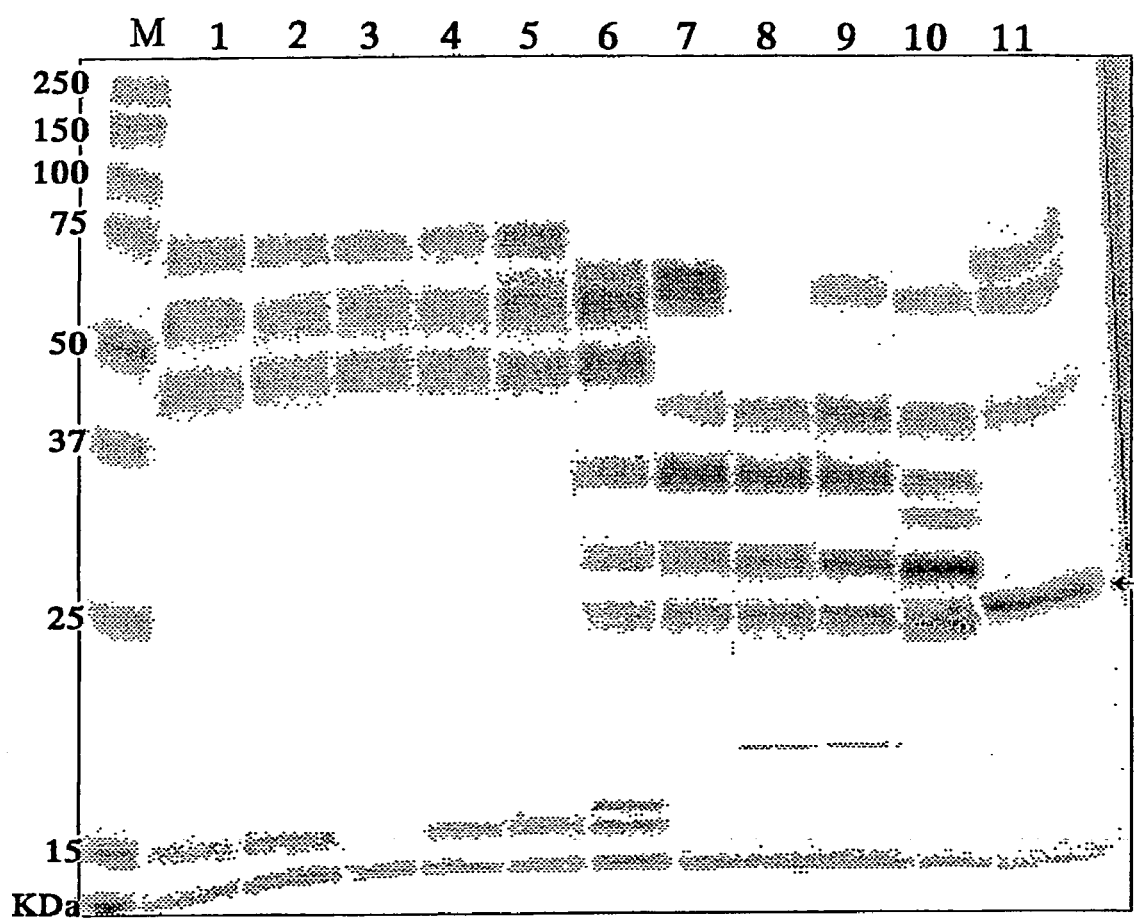
FIG. 2 shows the result of SDS-PAGE of the purified product (3 µg) at each step of purification process of UGPPase from kidney homogenate. In the figure: lane M; molecular weight marker, lane 1; kidney homogenate extract (0.00161 mU), lane 2; 30,000 g supernatant (0.00429 mU), lane 3; dialyzed sample (0.00481 mU), lane 4; 100,000 g supernatant (0.00579 mU), lane 5; Q-Sepharose column eluate (0.00655 mU), lane 6; second Q-Sepharose column eluate (0.0248 mU), lane 7; Q-Sepharose column eluate with an NaCl linear gradient (0.0523 mU), lane 8; Superdex200 column eluate (0.184 mU), lane 9; MonoQ column eluate (0.535 mU), lane 10; MonoP column eluate (2.59 mU), lane 11; native PAGE (98.5 mU).
Figure 3:
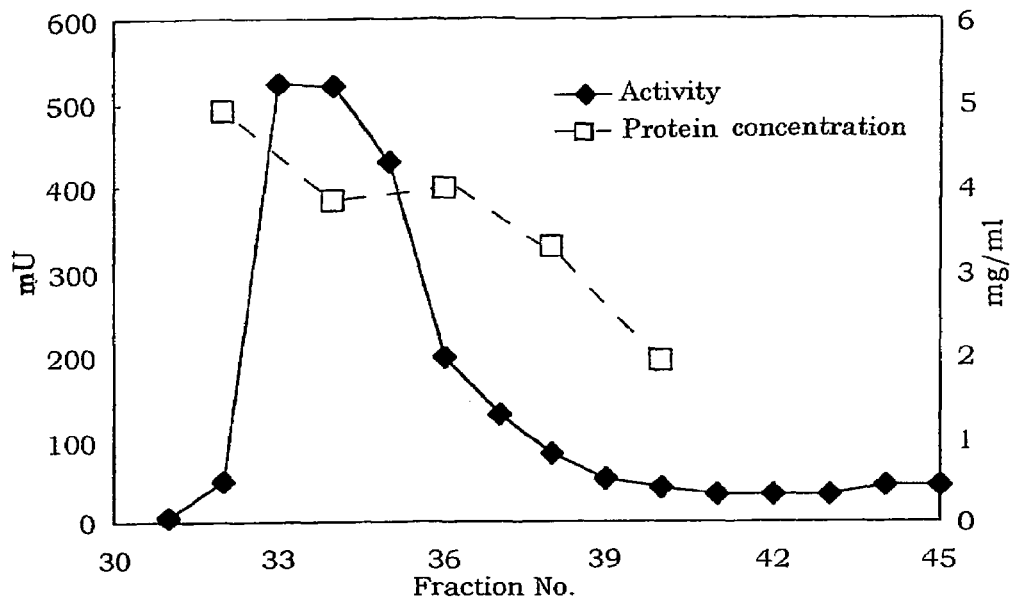
FIG. 3 is a graph showing protein concentration and UGPPase activity of fractions 31-45 from a MonoP column.
Figure 4:
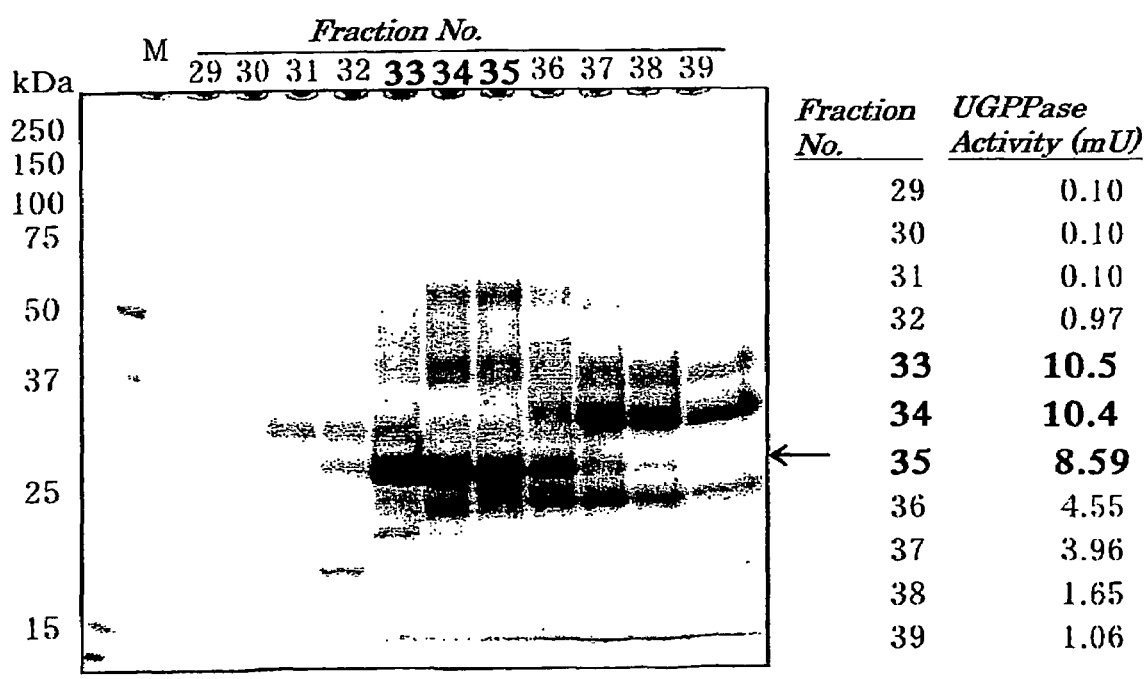
FIG. 4 shows a result of SDS-PAGE of fractions 29-39 from the MonoP column.
Figure 5:
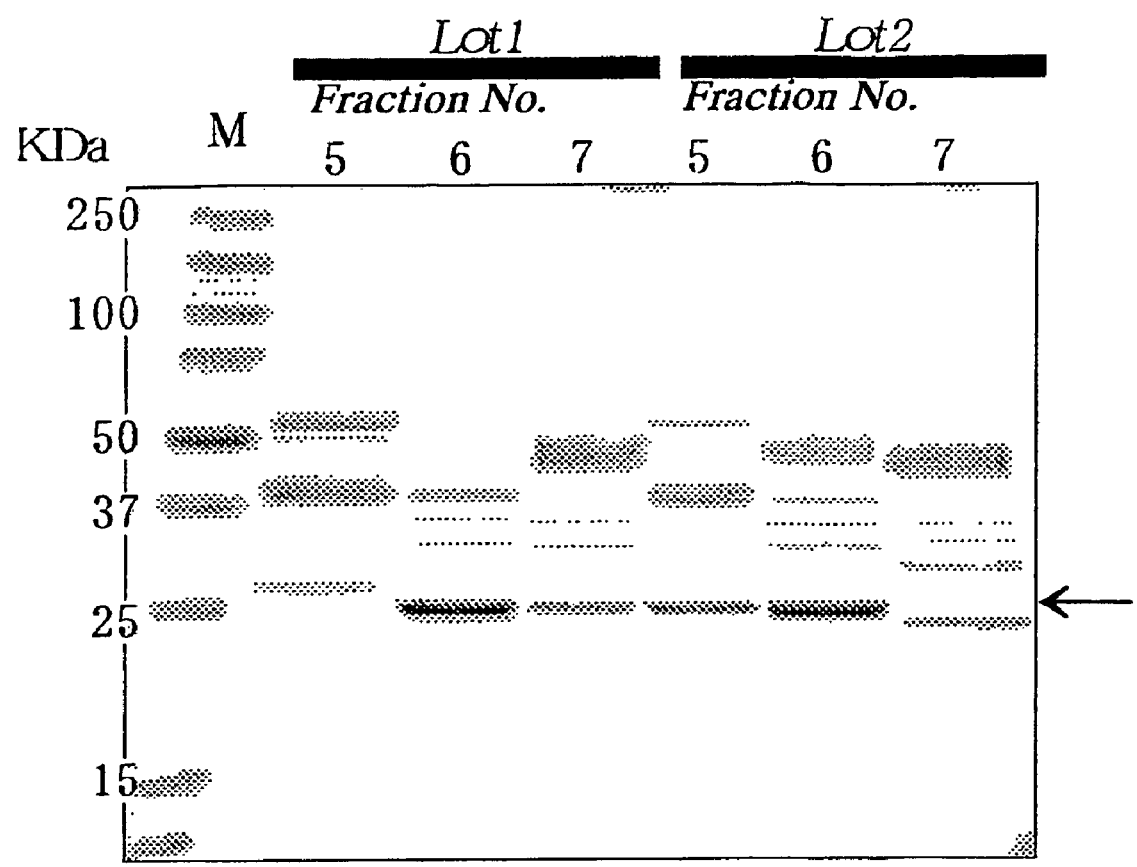
FIG. 5 shows a result of SDS-PAGE of two lots of samples after purification by native PAGE. In the figure: lane M; molecular weight marker. The amount of UGPPase in the gel: 0.184 mU (lot 1, fraction 5), 4.33 mU (lot 1, fraction 6), 2.88 mU (lot 1, fraction 7), 3.74 mU (lot 2, fraction 5), 4.43 mU (lot 2, fraction 6), 0.558 mU (lot 2, fraction 7).

Results:

(1) Purification of Porcine UGPPase:

Table 1 shows the UGPPase activity and its purity detected with the purified product at each purification step. FIG. 2 shows the result of SDS-PAGE of those samples. The specific activity of the final product eluted from the native PAGE, which had been purified approx. 60,000-fold, was 32 U/mg. This value was found largely comparable to the reported values of specific activity of the purified AGPPase from barley or *E. coli*, 23 U/mg or 9.5 U/mg, respectively, (13, 14). The single band detected on SDS-PAGE of the final purification product (FIG. 2) is concluded to be UGPPase, because of its identical behavior to the UGPPase-active band in the purification steps using MonoP (FIGS. 3 and 4) and native PAGE (FIG. 5), respectively.

TABLE 1

|  | Activity mU | Volume ml | Total activity mU | Protein conc. mg/ml | Specific activity mU/mg | Rec. % | Y % | P-fold |
| --- | --- | --- | --- | --- | --- | --- | --- | --- |
| Crude ext. 30,000 g | 6.86 | 12000 | 82269 | 12.80 | 0.54 | 100 | 100 | 1.00 |
| sup. | 18.72 | 10000 | 187217 | 13.10 | 1.43 | 248 | 228 | 2.67 |
| ppt. | 7.07 | 2350 | 16618 |  |  |  |  |  |
| Dialyzed 100,000 g | 16.67 | 13700 | 228408 | 10.40 | 1.60 | 122 | 278 | 2.99 |
| sup. | 16.02 | 10900 | 174671 | 8.30 | 1.93 | 84 | 212 | 3.61 |
| ppt. | 13.44 | 1200 | 16123 |  |  |  |  |  |
| Q-Sepharose |  |  |  |  |  |  |  |  |
| ○ | 3.08 | 24000 | 73926 | 1.41 | 2.18 | 84 | 90 | 4.08 |
| X | 2.00 | 36000 | 72054 |  |  |  |  |  |

TABLE 1-continued

| | Activity mU | Volume ml | Total activity mU | Protein conc. mg/ml | Specific activity mU/mg | Rec. % | Y % | P-fold |
|---|---|---|---|---|---|---|---|---|
| Re-Q-Sepharose | | | | | | | | |
| ○ | 12.14 | 1600 | 19426 | 1.47 | 8.26 | 60 | 24 | 15.42 |
| X | 4.37 | 5700 | 24936 | | | | | |
| Hydroxyapatite Q-Sepharose (linear gradient) | 10.31 | 1800 | 18562 | 0.59 | 17.42 | 96 | 23 | 32.52 |
| ○ | 121.86 | 110 | 13404 | 1.99 | 61.24 | 72 | 16 | 114.3 |
| X | 12.68 | 180 | 2283 | | | | | |
| Superdex200 | | | | | | | | |
| ○ | 63.28 | 250 | 15821 | 0.36 | 178.3 | 118 | 19 | 332.8 |
| X | 19.80 | 200 | 3960 | | | | | |
| MonoQ | | | | | | | | |
| ○ | 548.59 | 22.0 | 12069 | 1.93 | 284.2 | 76 | 15 | 530.7 |
| X | 15.39 | 27.5 | 423 | | | | | |
| MonoP | | | | | | | | |
| ○ | 2120.28 | 3.0 | 6361 | 2.46 | 861.9 | 53 | 8 | 1609 |
| X | 118.18 | 5.0 | 591 | | | | | |
| Native PAGE | | | | | | | | |
| ○ | 876.28 | 2.5 | 2191 | 0.03 | 32819 | 34 | 3 | 61275 |
| X | 6.10 | 0.5 | 3 | | | | | |

R; recovery, Y; yield, P; purification rate, sap.; supernatant, ppt. precipitate, ○; used in the next step, X; not used (2) ESI-TOF MS/MS Analysis of Porcine UGPPase:

Seven peptide fragments prepared by trypsin treatment of the final purification product were analyzed by ESI-TOF MS/MS for amino acid sequencing. The sequences thus known (SEQ ID NOs: 5, 6, 7 and 8) were found to be highly homologous to four regions of human and mouse proteins, respectively, with unknown function (FIGS. 6 and 7). The human and mouse proteins, ID numbers AAD15563.1 (NCBI accession No. AF111170) (SEQ ID NO:3) and BAB23110.1 (NCBI accession No. AK003991) (SEQ ID NO:4), respectively, were considered to be enzymes, as they had a Nudix (nucleoside diphosphate linked to some other moiety, X)-like hydrase motif (24). The purified porcine UGPPase protein was considered to be a porcine homologue to these human and mouse proteins, which are approximately 80% homologous with each other.

Figure 12:
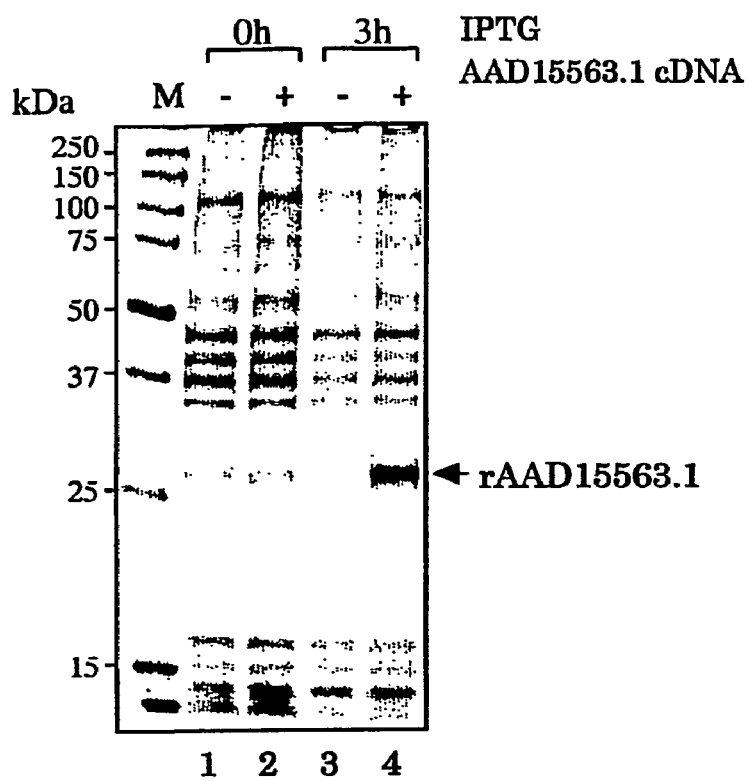
FIG. 12 shows the results of SDS-PAGE of the suspension of the AD494(DE3) cells transformed with pET11a-AAD15563.1 or pET11a: lane 1; 0-hour culture of pET11a-transformed cells, lane 2; 0-hour culture of pET11a-AAD15563.1-transformed cells, lane 3; 3-hour culture of pET11a-transformed cells, lane 4; 3-hour culture of pET11a-AAD15563.1-transformed cells. The amount applied to the gel: 0.072, 0.034, 0.034 and 0.292 (mU) for lanes 1 to 4, respectively.
Figure 13:
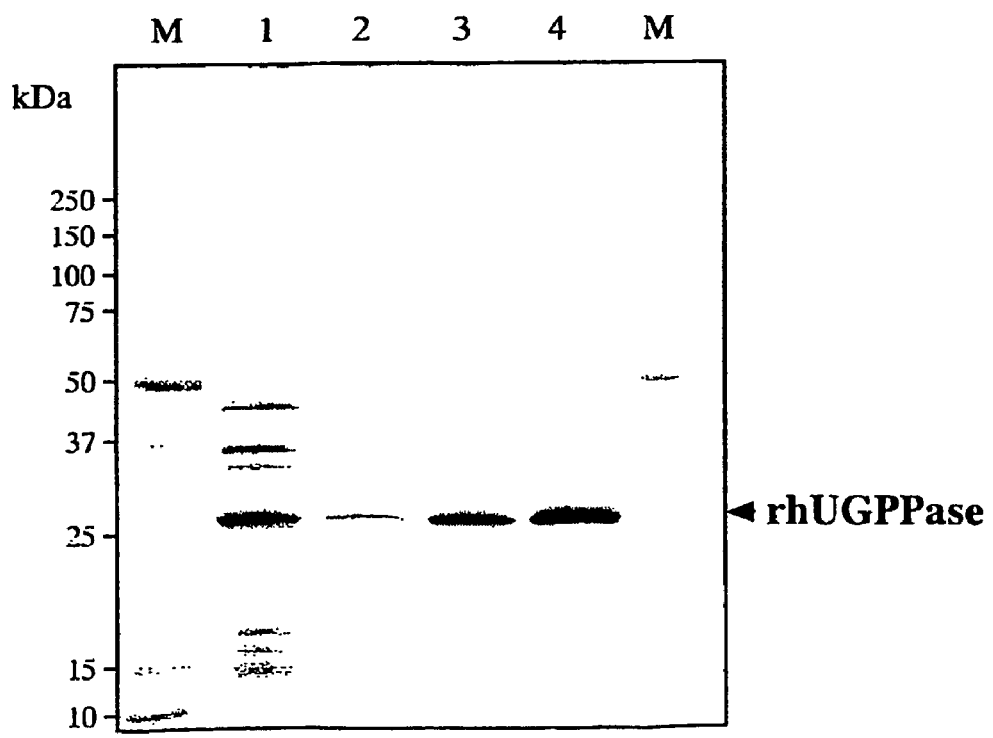
FIG. 13 shows the results of SDS-PAGE (10-20% polyacrylamide gel) performed with each of the purified products (2.0 μg) at the purification steps of the recombinant human UGPPase (r-hUGPPase). In the figure: lane 1; AD494(DE) suspension (1.8 mU), lane 2; 10,000 g supernatant (3.0 mU), lane 3; Q-Sepharose eluate (6.2 mU), lane 4; MonoP eluate (13.5 mU). Specific activity of the samples were: lane 1; 0.910 U/mg, lane 2; 1.51 U/mg, lane 3; 3.09 U/mg, lane 4; 6.74 U/mg.

(3) Activity Measurement of the Recombinant AAD15563.1 and its Purification:

The DNA coding for AAD15563.1, which was now considered to be a human UGPPase based on the above results of the ESI-TOF MS/MS, was amplified by PCR and cloned into an expression vector (FIG. 10), and expressed recombinant protein then was confirmed to have UGPPase activity. Primers for this PCR were designed according to the nucleotide sequence (SEQ ID NO:1) reported by the NCBI (the National Center for Biotechnology Information). The amplified DNA was cloned into the E. coli expression vector pET11a to obtain a plasmid, pET11a-AAD15563.1. This plasmid was introduced into E. coli AD494 cells. The suspension of the transformed E. coli AD494(DE3) cells expressing the introduced gene exhibited 8 times higher UGPPase activity compared with the suspension of the control bacteria that had simply received the intact plasmid, pET11a (FIG. 12). SDS-PAGE (polyacrylamide 10-20%) of the suspension of the transformed bacteria confirmed the band of the expressed protein, (FIG. 12). The results of SDS-PAGE (FIG. 13) and UGPPase activity measurement of the suspension of the E. coli AD494(DE3) cells expressing AAD15563.1, its soluble fractions after sonication, and the Q-Sepharose- and MonoP-purified products, respectively, indicated that the specific activity of the UGPPase rose in parallel with the increasing strength of the band. The specific activity of the final product, which exhibited a single band on SDS-PAGE, was 6.7 U/mg, a value comparable to that of the final purified porcine UGPPase. These results indicate that the protein AAD15563.1 is a human UGPPase.

Figure 14:
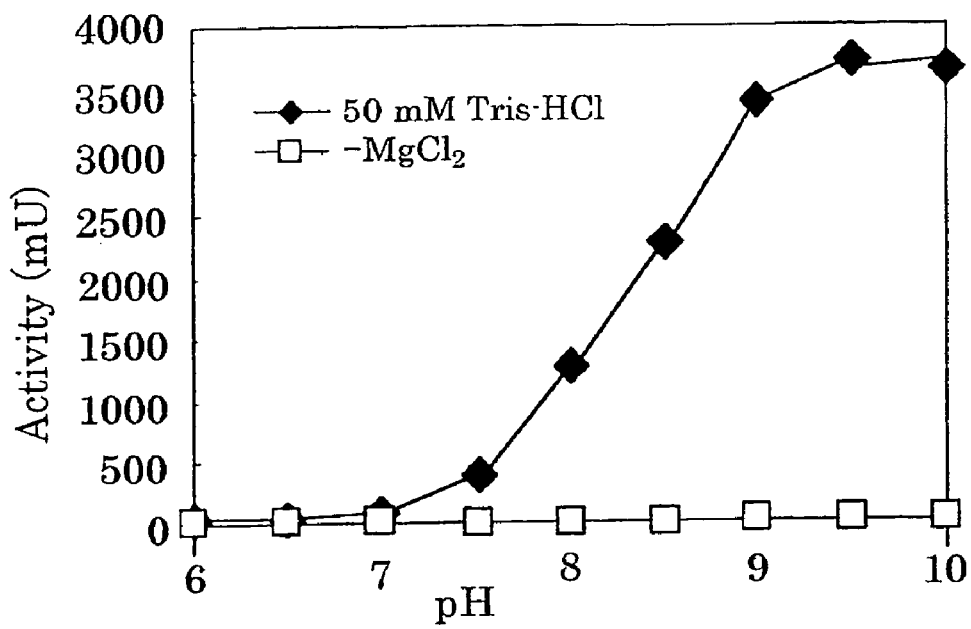
FIG. 14 is a graph showing the optimal pH range for porcine UGPPase. The measurement was conducted in 50 mM Tris-HCl with (♦) or without (□) MgCl$_2$.
Figure 15:
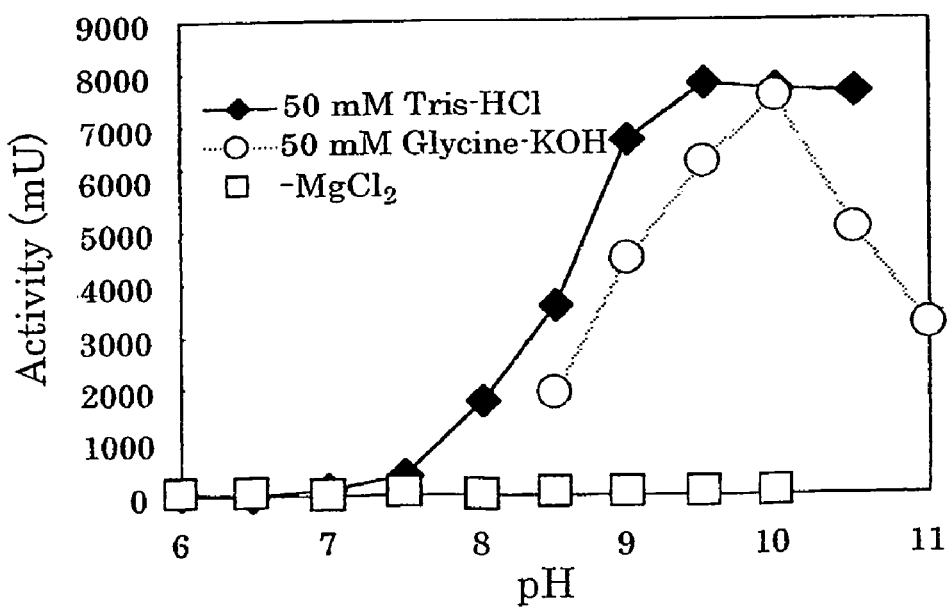
FIG. 15 is a graph showing the optimal pH range for human recombinant UGPPase. The measurement was conducted in 50 mM Tris-HCl with (♦) or without (□) 20 mM MgCl$_2$, or in 50 mM Glycine-KOH (○) with 20 mM MgCl$_2$.
Figure 16:
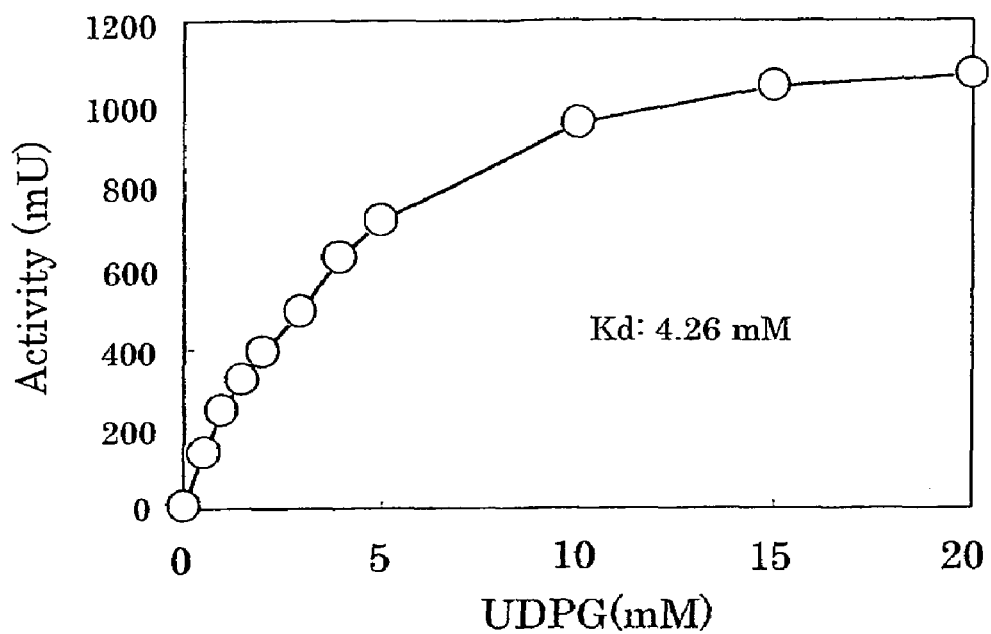
FIG. 16 is a graph showing the activity of porcine UGPPase as a function of UDPG concentration (mM). From the graph, Kd of the enzyme is determined to be 4.26 mM.
Figure 17:
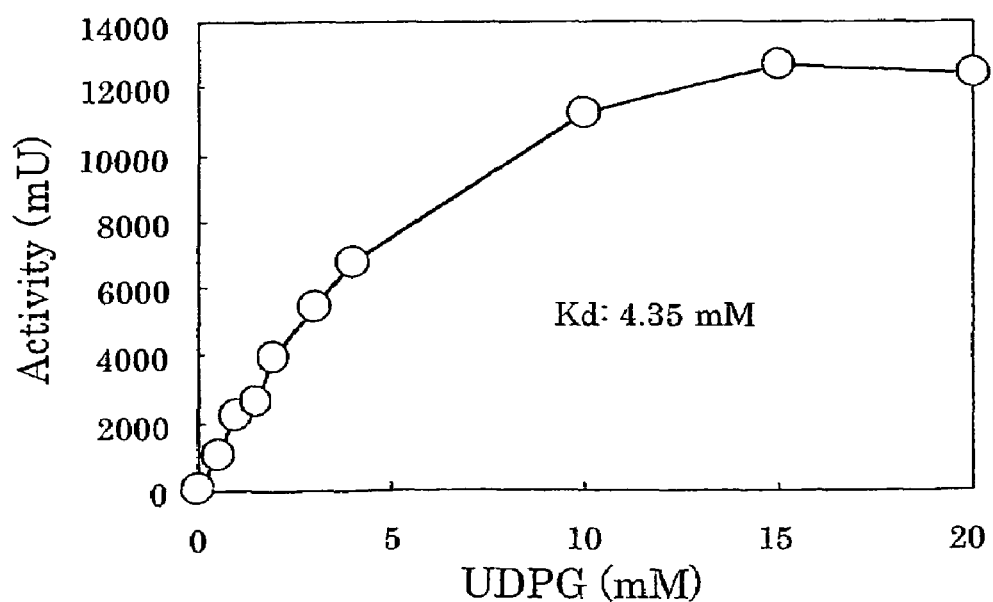
FIG. 17 is a graph showing the activity of human recombinant UGPPase as a function of UDPG concentration (mM). From the graph, Kd of the enzyme is determined to be 4.35 mM.

(4) Characterization of Human and Porcine UGPPase:

Using the human and porcine UGPPase final purified products, a study was carried out to know the optimal conditions for their enzymatic activity. The results showed that the both enzymes have their optimal pH in the range from 9.5 to 10 and be $Mg^{2+}$-dependent (FIGS. 14 and 15). The Kd (dissociation constant) of the enzymes with the substrate UDPG was determined to be 4.35 mM and 4.26 mM for human and porcine UGPPase, respectively, indicating their almost equal affinity for the substrate (FIGS. 16 and 17). Among ADPG, UDPG and GDPG, the human and porcine UGPPase both exhibited the highest substrate specificity to UDPG: in the presence of 5 mM of a corresponding substrate, their relative activity was measured to be only about 20 and 10% with ADPG and GDPG, respectively, as compared with the activity with UDPG (100%) (Tables 2 and 3).

TABLE 2

| (a) Porcine UGPPase | |
|---|---|
| Substrates | % activity with respect to UDPG |
| UDPG | 100 |
| UDP-glucuronic | bdl |

TABLE 2-continued (a) Porcine UGPPase

| Substrates | % activity with respect to UDPG |
|---|---|
| UDP-galactose | bdl |
| ADPG | 20 |
| ADP-ribose | 95 |
| GDPG | 10 |
| CDPG | 2 |
| ATP | bdl |
| UTP | bdl |
| AMP | bdl |
| UTP | bdl |
| ADP | bdl |
| NAD | bdl |
| Bis-PNPP | bdl |
| PNPP | bdl | bdl: below detection limit

TABLE 3

(a) human UGPPase

| Substrates | % activity with respect to UDPG |
|---|---|
| UDPG | 100 |
| UDP-glucuronic | bdl |
| UDP-galactose | bdl |
| ADPG | 15 |
| ADP-ribose | 110 |
| GDPG | 10 |
| CDPG | 3 |
| ATP | bdl |
| UTP | bdl |
| AMP | bdl |
| UTP | bdl |
| ADP | bdl |
| NAD | bdl |
| Bis-PNPP | bdl |
| PNPP | bdl | bdl: below detection limit (5) Northern Blot Analysis of Normal Tissues from Pig and Human Adult.

Figure 18:
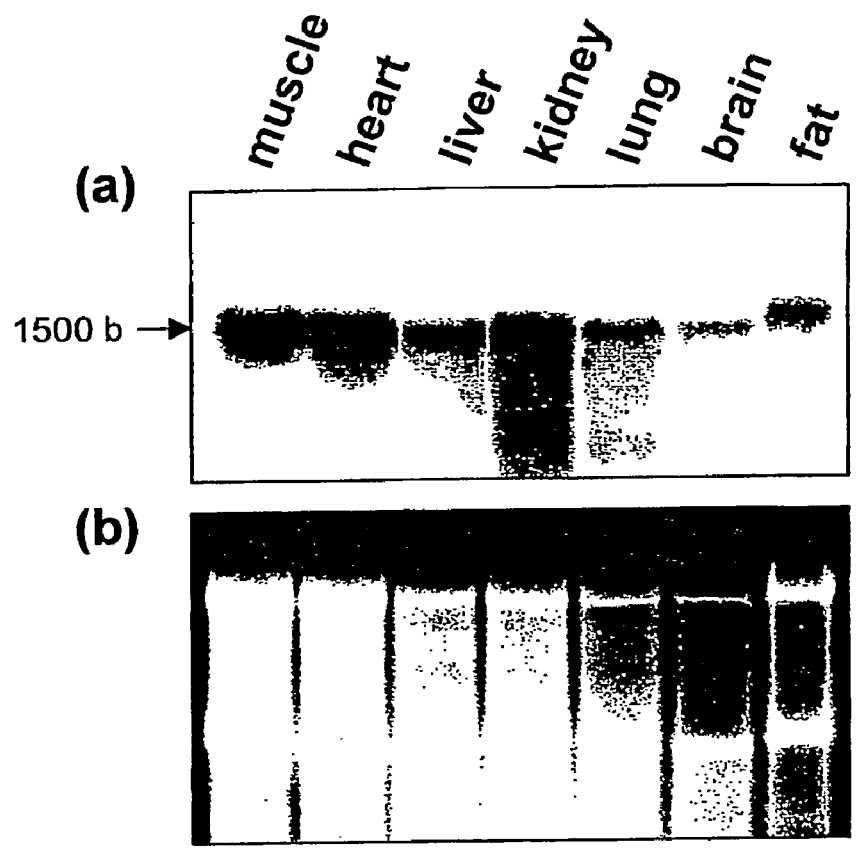
FIG. 18 shows the result of Northern blot analysis of the total RNA from pig tissues.
Figure 19:
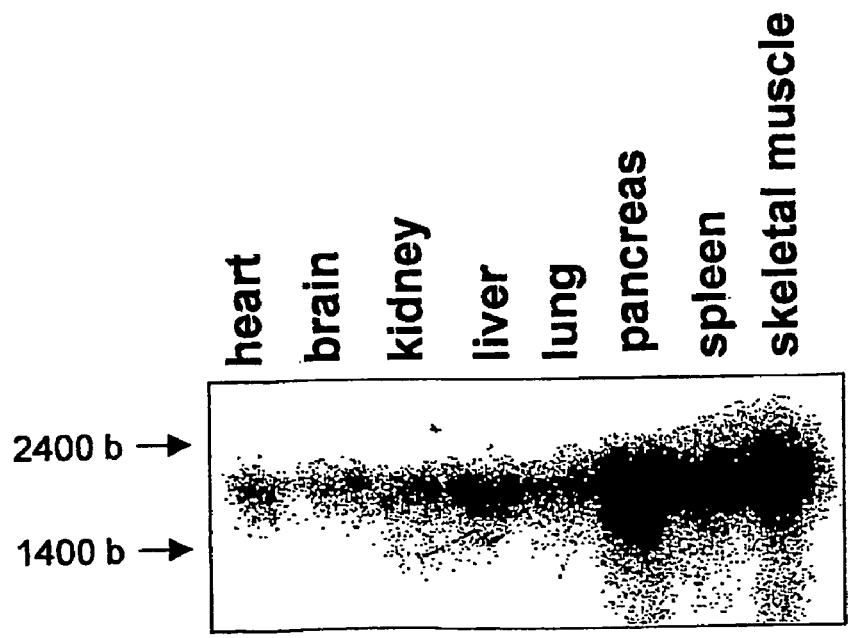
FIG. 19 shows the result of Northern blot analysis of the total RNA from human tissues.

FIGS. 18 and 19 shows the result of Northern blot analysis of the total RNA from tissues of pig and adult human, respectively. It is seen that UGPPase mRNA occurs in different tissue examined.

Figure 20:
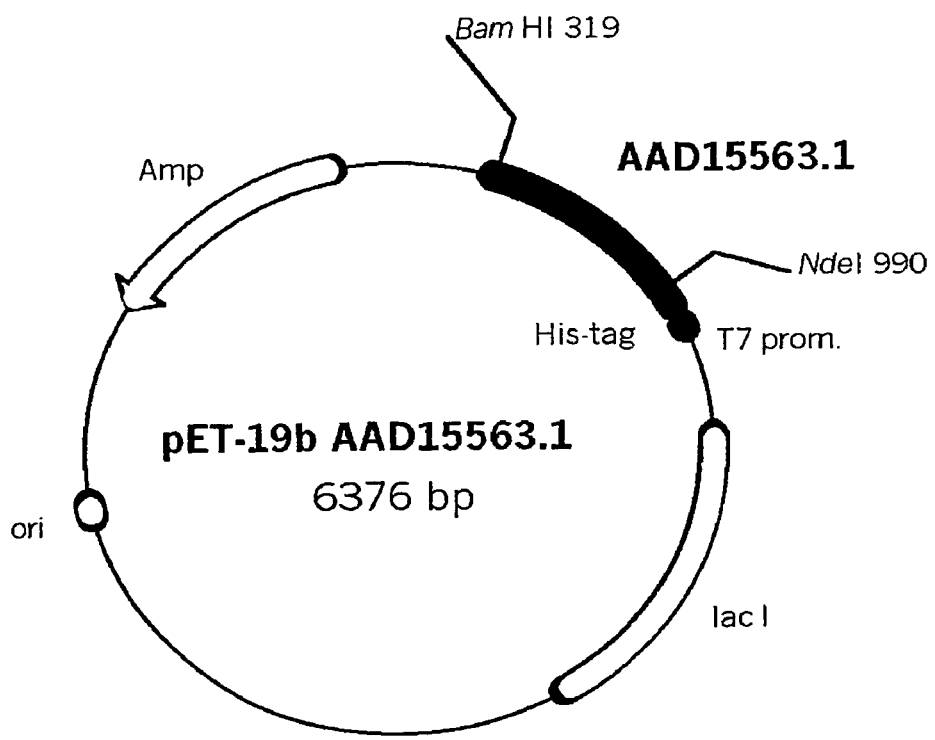
FIG. 20 illustrates a pET19b with incorporated AAD15563.1.
Figure 21:
FIG. 21 shows the result of the electrophoresis, (0.8% agarose) of the NdeI/BamHI-digested pET19b.AAD 15563.1.
Figure 22:
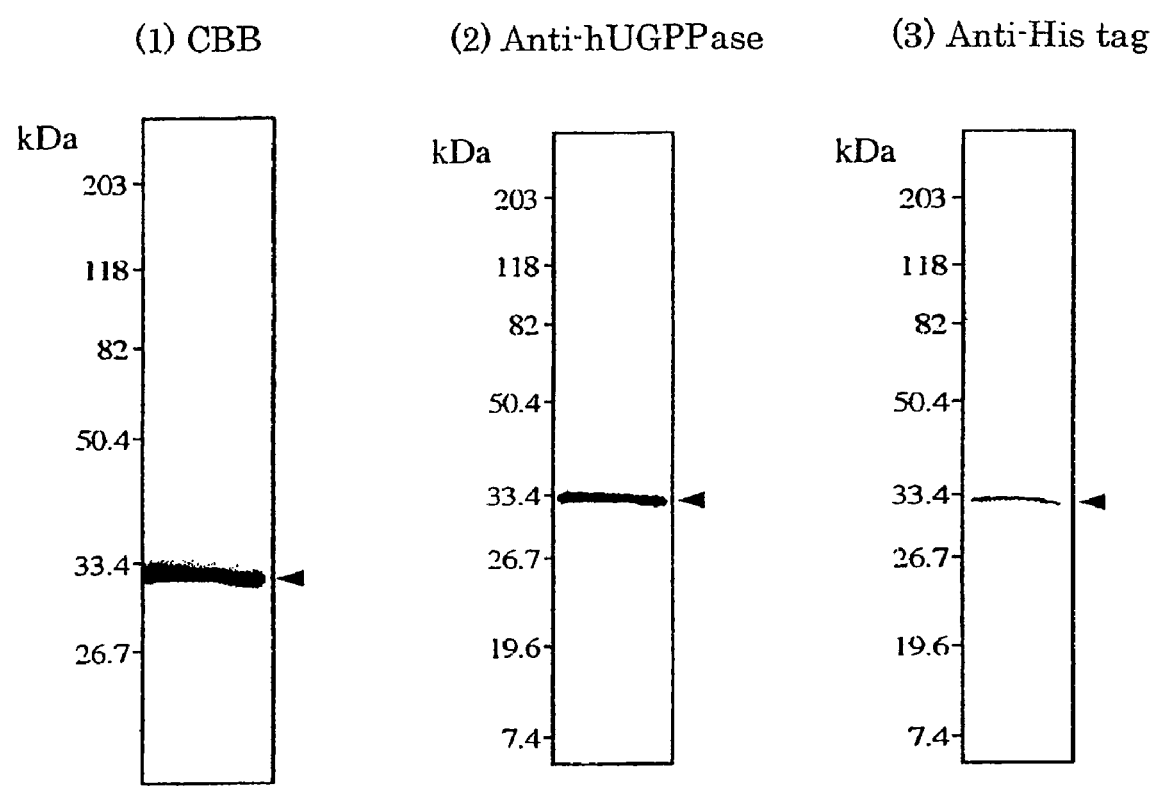
FIG. 22 shows the results of CBB staining (1), and Western blot analysis of hUGPPase His-tag fusion protein expressed in and purified from transformed *E. coli* cells, with anti-hUGPPase antiserum (2) and with an anti-His tag antibody (3).

(6) Construction of pET-19b AAD15563.1 and Purification of hUGPPase His-tag Fusion Protein FIGS. 20 and 21 show the expression vector pET-19b AAD15563.1 and result of its agarose gel electrophoresis after digestion with and NdeI and BamHI. *E. coli* AD494 (DE3) cells transformed with this plasmid was found to express a large amount of His-tag fusion protein. The Western blot analysis of the final, purified product obtained in (11) above confirmed that the protein was the hUGPPase His-tag fusion protein (FIG. 22).

(7) hUGPPase ELISA

Figure 23:
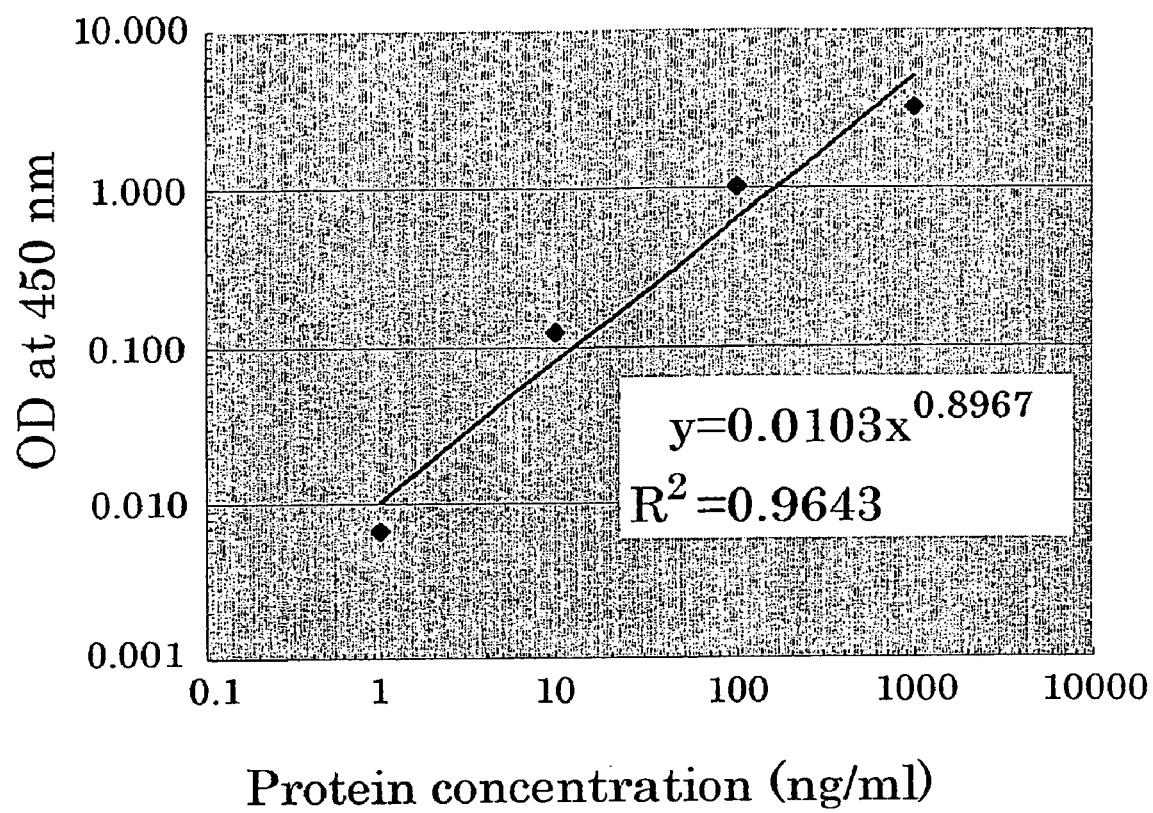
FIG. 23 is a graph showing the results of hUGPPase ELISA of purified hUGPPase His-tag fusion protein as a standard. OD at 450 nm for standard solutions containing the protein at 1-1,000 ng/ml are plotted. The oblique line indicates linearization of the relation between of protein concentration (x) and OD 450 (y), both in logarithmic scale.

An ELISA detection system was established employing a rabbit anti-hUGPPase antibody as the solid phase and purified hUGPPase His-tag fusion protein as the standard. The EC50 (effecter concentration for half-maximum response) of this system was determined to be 246.8 ng/ml, with the lowest detection limit of 10 ng/ml and the range of measurement of 10-1,000 ng/ml (FIG. 23).

Figure 24:
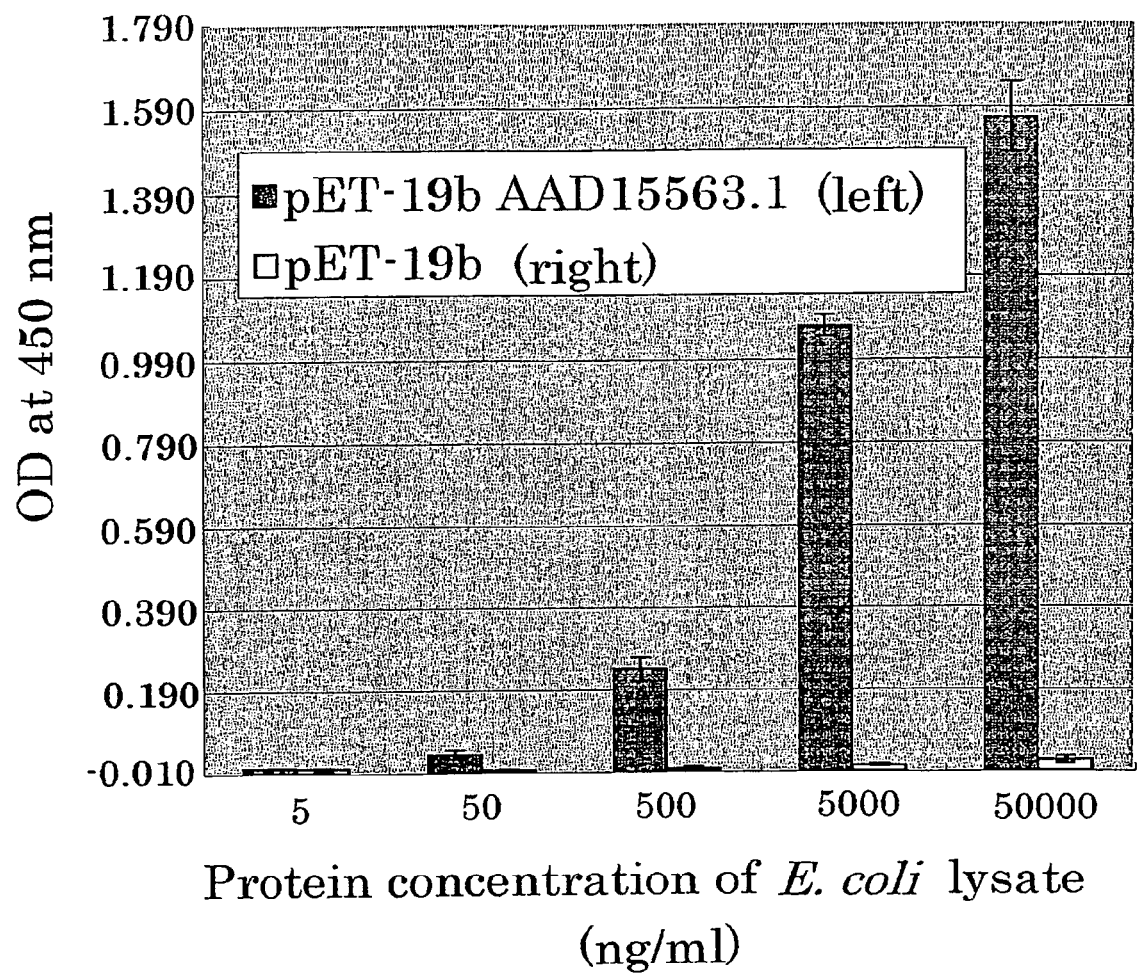
FIG. 24 is a graph showing the results of hUGPPase ELISA of lysates of two types of *E. coli* cells, one harboring pET-19b AAD15563.1 and the other pET-19b, at different levels of dilution.

The ELISA performed with the lysates of *E. coli* AD494 (DE3) cells harboring plasmid pET-19b AAD15563.1 showed a protein concentration-dependent increase in OD at 450 nm, whereas there was no notable increase in OD at 450 with the *E. coli* AD494(DE3) cells harboring nothing more than plasmid pET-19b (FIG. 24) lysates. The results indicate that the ELISA system established above has high specificity to hUGPPase without exhibiting any cross-reaction with *E. coli* intrinsic proteins.

(8) Determination of UDPG in a Sample

The amount of UDPG contained in a sample was determined following the procedure described above in "Materials and Methods" section. The results are shown in Table 4 and FIG. 25. The measured amount of G1P (nmol), which is regarded as being equal to the amount of UDPG, exhibited sufficient correlation with the amount of UDPG initially contained in the sample, allowing determination of UDPG amount in the sample.

TABLE 4

| UDPG in the Sample in the assay cuvette (nmol) | UDPG determined as G1P produced (nmol) |
|---|---|
| 6.0 | 8.4 ± 2.92 |
| 9.0 | 11.8 ± 4.11 |
| 10.0 | 14.4 ± 3.35 |
| 15.0 | 15.4 ± 5.57 |
| 22.5 | 17.8 ± 4.93 |
| 30.0 | 25.7 ± 6.38 |
| 45.0 | 33.3 ± 3.07 |
| 60.1 | 48.2 ± 4.68 |
| 90.1 | 108.5 ± 15.96 |
| 150.2 | 147.4 ± 28.62 |
| 300.3 | 249.9 ± 30.60 |

INDUSTRIAL APPLICABILITY

The present invention enables to provide UGPPase in a purified form, and in any desired scale. The purified enzyme thus provided can be utilized to determine UDPG levels in samples such as blood. In addition, the purified enzyme is used, for example, as the reference standard product in the field of biochemical assay of a variety of samples including natural, biological specimens, for the measurement of activity levels of the enzyme. The use of the reference standard allows to obtain standardized data of the activity levels of the enzyme, which enables exactly quantitative comparison among the data taken from different samples measured at different times and places. The present invention also provides an anti-UGPPase antibody, as well as a method for enzyme-linked immunosorbent assay (ELISA) based on the anti-UGPPase antibody, which is useful for measurement and/or detection of UGPPase in a variety of samples and may also be used to provide an ELISA kit for measurement of UGPPase. Further, the present invention is also used for the determination of UDPG in a sample, such as blood.

REFERENCES

1. Preiss, J. & Romeo, T. (1994) Prog. Nucleic Acid Res. Mol. Biol. 47:301-327.
2. Liu, M. Y., Yang, H. & Romeo, T. (1995) J. Bacteriol. 177: 2663-2672.
3. Bollen, M., Keppens, S. & Stalmans, W. (1998) Biochem. J. 336: 19-31
4. Pozueta-Romero, J., Perata, P. & Akazawa, T. (1999) Crit. Rev. Plant Sci. 18:489-525.
5. Gaudet, G., Forano, E., Dauphin, G. & Delort, A. M. (1992) Eur. J. Biochem. 207:155-162.

6. Belanger, A. E. & Hatfull, G. F. (1999) J. Bacteriol. 181:6670-6678.
7. Guedon, E., Desvaux, M. & Petitdemange, H. (2000) J. Bacteriol. 182: 2010-2017.
8. David, M. Petit, W. A., Laughlin, M. R., Shulman, R. G., King, J. E. & Barrett, E. J. (1990) J. Clin. Invest. 86:612-617.
9. Pozueta-Romero, J. & Akazawa, T. (1993) J. Exp. Bot. 44, Suppl: 297-304.
10. Massillon, D., Bollen, M., De Wulf, H., Overloop, K., Vanstapel, F., Van Hecke, P. & Stalmans, W. (1995) J. Biol. Chem. 270: 19351-19356.
11. Rodriguez-Lopez, M., Baroja-Fernandez, E., Zandueta-Criado, A., Pozueta-Romero, J. (2000) Proc. Natl. Acad. Sci. USA 97:8705-8710.
12. Rodrigues-Lopez, M., Baroja-Fernandez, E., Zuandueta-Criado A., Moreno-Bruna, B., Munoz, F. J., Akazawa, T., & Pozueta-Romero, J. (2001) FEBS Lett., 490:44-48.
13. Moreno-Bruna, B., Baroja-Fernandez, E., Jose Munoz, F., Bastarrica-Berasategui, A., Zandueta-Criado, A., Rodriguez-Lopez, M., Lasa, I., Akazawa, T. & Pozueta-Romero, J. (2001) Proc. Natl. Acad. Sci. USA 98:8128-8132.
14. Schliselfeld, L. H., van Eys, J. & Touster, O. (1965) J. Biol. Chem. 240, 811-818
15. Skidmore, J. & Trams, E. G. (1970) Biochim. Biophys. Acta 219, 93-103
16. Bachorik, P. S. & Dietrich, L. S. (1972) J. Biol. Chem. 247, 5071-5078
17. Fukui, S., Yoshida, H., Tanaka, T., Sakano, T., Usui, T. & Yamashina, I. (1981) J. Biol. Chem. 256, 10313-10318
18. van Dijk, W., Lasthuis, A-M., Trippelvitz, L. A. W. & Muilerman, H. G. (1983) Biochem. J. 214, 1003-1006
19. Hickman, S., Wong-Yip, Y. P., Rebee, N. F. & Greco, J. M. (1985) J. Biol. Chem. 260, 6098-6106
20. Yano, T., Horie, K., Kanamoto, R., Kitagawa, H., Funakoshi, I. & Yamashina (1987) Biochem. Biophys. Res. Commun. 147, 1061-1069
21. Harper, G. S., Hascall, V. C., Yanagishita, M. & Gahl, W. A. (1987) J. Biol. Chem. 262, 5637-5643
22. Johnson, K., Vaingankar, S., Chen, Y., Moffa, A., Goldring, M. B., Sano, K., Jin-Hua, P., Sali, A., Goding, J. & Terkeltaub, R. (1999) Arthritis Rheum. 42, 1986-1997
23. Hames, B. D. (1990) One-dimensional polyacrylamide gel electrophoresis, in Gel electrophoresis of proteins (Hames, B. D. and Rickwood, D. eds.), pp. 1-139, Oxford University Press
24. Bessman, M. J., Frick, D. N. & O'Handley, S. F. (1996) J. Biol. Chem. 271:25059-25062.
25. Spiro, M. J. (1984) Effect of diabetes on the sugar nucleotides in several tissues of the rat, Diabetologia 26, 70-75
26. Sochor, M., Kunjara S., Baquer, N. Z. and McLean P. (1991) Regulation of glucose metabolism in livers and kidneys of NOD mice, Diabetes 40, 1467-1471
27. Robinson K., Wenstein, M. L., Lindenmayer, G. E. and Buse, M. G. (1995) Diabetes 44, 1438-1446
28. Laughlin, M. R., Petit, W. A., Dizon, J. M., Shulman, R. G. and Barrett, E. J. (1988) NMR measurement of in vivo myocardial glycogen metabolism, J. Biol. Chem. 263, 2285-2291
29. Seoane, J., Trinh, K., O'Doherty, R. M., Gomez-Foix, A. M., Lange, A. J., Newgard, C. B. and Guinovart, J. J. (1997) Metabolic impact of adenovirus-mediated overexpression of the glucose-6-phosphate catalytic subunit in hepatocytes, J. Biol. Chem. 272, 26962-26977

We claim:

1. An isolated protein which consists of the amino acid sequence set forth in SEQ ID NO: 2 which has an activity of hydrolyzing UDP-glucose into glucose-1-phosphate and uridine 5'-monophosphate.

2. A recombinant protein which consists of the amino acid sequence set forth in SEQ ID NO: 2 which has an activity of hydrolyzing UDP-glucose into glucose-1-phosphate and uridine 5'-monophosphate.

3. A method for assaying UGPPase activity in a sample comprising comparing said UGPPase activity in said sample to a reference standard, wherein the reference standard is a recombinant protein consisting of the amino acid sequence set forth in SEQ ID NO: 2.

4. An isolated protein which is encoded by the polynucleotide sequence set forth in SEQ ID NO: 1.

5. The isolated protein of claim 4 which has an activity of hydrolyzing UDP-glucose into glucose-1-phosphate and uridine 5'-monophosphate.

6. A composition comprising the isolated protein of claim 1 and an acceptable buffer.

7. A composition comprising the recombinant protein of claim 2 and an acceptable buffer.

8. A fusion protein which consists of the amino acid sequence set forth in SEQ ID NO: 2 and a tag.

9. The fusion protein of claim 8 wherein the tag is a histidine tag.

10. An antigen column which comprises the protein of claim 2 and an activating material wherein said protein is bound to said activating material.

11. An antigen column which comprises the fusion protein of claim 8 and an activating material wherein said fusion protein is bound to said activating material.

12. The method of claim 3, comprising measuring amount/rate of formation of glucose-1-phosphate and/or uridine 5'-monophosphate in said sample versus said standard.

13. The method of claim 12, comprising measuring amount/rate of formation of glucose-1-phosphate in said sample versus said standard.

* * * * *